(12) United States Patent
Wang et al.

(10) Patent No.: US 11,994,457 B2
(45) Date of Patent: May 28, 2024

(54) METHODS FOR DETECTION OF SILVER NANOPARTICLES

(71) Applicant: City University of Hong Kong, Hong Kong (HK)

(72) Inventors: Wenxiong Wang, Hong Kong (HK); Anqi Sun, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 112 days.

(21) Appl. No.: 17/585,781

(22) Filed: Jan. 27, 2022

(65) Prior Publication Data
US 2023/0236106 A1 Jul. 27, 2023

(51) Int. Cl.
*G01N 15/1434* (2024.01)
*C12Q 1/02* (2006.01)
*G01N 15/10* (2006.01)

(52) U.S. Cl.
CPC ........... *G01N 15/1434* (2013.01); *C12Q 1/02* (2013.01); *G01N 2015/1006* (2013.01)

(58) Field of Classification Search
None
See application file for complete search history.

(56) References Cited

PUBLICATIONS

Lachance, M.-A. Yeast biodiversity: How many and how much? In.: The Yeast Handbook. Rosa, C. and Gabor, P. (eds). Chapter 1. Copyright 2006 Springer-Verlag Berlin Heidelberg, pp. 1-9; specif. p. 4 (Year: 2006).*
Kurtzman, C.P., Fell, J.W. and Boekhout, T. (eds). The Yeasts, A taxonomic study. vol. 1. Copyright 2011 Elsevier B.V. Index to taxa by genus and species, pp. i1-i23; specif. pp. i16, i17 (Year: 2011).*
Piddington, D.L. 2000. Growth of *Mycobacterium tuberculosis* in a defined medium is very restricted by acid pH and Mg2+ levels. Infection and Immunity 68(8): 4518-4522; specif. p. 4518 (Year: 2000).*
Amberg, D.C. et al. 2005. Measuring yeast cell density by spectrophotometry. In: Methods in Yeast Genetics, 2005 edition, Techniques and Protocols 16. Cold Spring Harbor Laboratory Press, Cold Spring Harbor, NY. p. 1 (Year: 2005).*
Angel. et al., The impact of size on the fate and toxicity of nanoparticulate silver in aquatic systems, Elsevier, Ltd., Chemosphere, vol. 93 (2013), pp. 359-365, http://dx.doi.org/10.1016/j.chemosphere.2013.04.096 2013.
Axson, et al., Rapid Kinetics of Size and pH-Dependent Dissolution and Aggregation of Silver Nanoparticles in Simulated Gastric Fluid, American Chemical Society, The Journal of Physical Chemistry, vol. 119, pp. 20632-20641 2015.
Bao, et al., Characterization of Silver Nanoparticles Internalized by *Arabidopsis* Plants Using Single Particle ICP-MS Analysis, Frontiers in Plant Science, vol. 7, Article 32 Feb. 1, 2016.
Benn, et al., Nanoparticle Silver Released into Water from Commercially Available Sock Fabrics, American Chemical Society, Environ. Sci. Technol., vol. 42, pp. 4133-4139 2008.
Blaser, et al., Estimation of cumulative aquatic exposure and risk due to silver: Contribution of nano-functionalized plastics and textiles, Elsevier, Science Direct, vol. 390, pp. 396-409 2008.
Chao, et al., Speciation Analysis of Silver Nanoparticles and Silver Ions in Antibacterial Products and Environmental Waters via Cloud Point Extraction-Based Separation, ACS Publications, American Chemical Society, Analytical Chemistry, vol. 83, pp. 6875-6882 2011.
Chan, et al., Organelle Size Scaling of the Budding Yeast Vacuole Is Tuned by Membrane Trafficking Rates, Biophysical Journal, vol. 106, pp. 1986-1996 May 2014.
Choi, et al., Role of sulfide and ligand strength in controlling nanosilver toxicity, Elsevier, Water Research, vol. 43, pp. 1879-1886 2009.
Fabricius, et al., ICP-MS-based characterization of inorganic nanoparticles—sample preparation and off-line fractionation strategies, Anal Bioanal Chem, vol. 406., pp. 467-479 2014.
Cvjetko, et al., Phytotoxic effects of silver nanoparticles in tobacco plants, Environmental Science and Pollution Research, vol. 25, pp. 5590-5602, https://doi.org/10.1007/s11356-017-0928-8 2018.
Gliga, et al., Size-dependent cytotoxicity of silver nanoparticles in human lung cells: the role of cellular uptake, agglomeration and Ag release, BioMed Central, Particle and Fibre Toxicology, vol. 11, p. 11, http://www.particleandfibretoxicology.com/content/11/1/11 2014.
Lee, et al., Nanoparticle Size Detection Limits by Single Particle ICP-MS for 40 Elements, ACS Publications, American Chemical Society, Environmental Science & Technology, vol. 48, pp. 10291-10300 2014.
Hadioui, et al., Improvements to Single Particle ICPMS by the Online Coupling of Ion Exchange Resins, ACS Publications, American Chemical Soceity, Analytical Chemistry, vol. 86, pp. 4668-4674 2014.
Li, et al., The yeast lysosome-like vacuole: Endpoint and crossroads, Elsevier, Biochimica et Biophysica Acta, vol. 1793, pp. 650-663 2009.

(Continued)

*Primary Examiner* — Adam Weidner
*Assistant Examiner* — Sharon M. Papciak
(74) *Attorney, Agent, or Firm* — Melvin Li; Heslin, Rothenberg Farley & Mesiti PC

(57) ABSTRACT

A method for detection of the presence and/or quantities of silver nanoparticles in a specimen is shown. The method includes the steps of a) providing a detection organism suspended in a medium, b) treating the detection organism with zinc ions thus effecting auto-fluorescence therefrom, and then measuring degree of fluorescence of the detection organism suspended medium, c) adding the specimen to the detection organism suspended medium, treating the detection organism therein with the specimen for a period of time, and measuring change of fluorescence of the detection organism-suspended medium over time, d) calculating amount of silver ions intracellularly dissolved from the silver nanoparticles and accumulated in the detection organism in view of the change of fluorescence, and e) extrapolating quantity of silver nanoparticles in the specimen in view of the change of fluorescence and the amount of the intracellularly dissolved silver ions.

10 Claims, 21 Drawing Sheets

(56) References Cited

PUBLICATIONS

Levard, et al., Environmental Transformations of Silver Nanoparticles: Impact on Stability and Toxicity, ACS Publications, American Chemical Society, Environmental Science & Technology, vol. 46, pp. 6900-6914 2012.

Liu, et al., Highly sensitive and selective colorimetric detection of Ag(I) ion using 3,3', 5,5',-tetramethylbenzidine (TMB) as an indicator, Elsevier, Sensors and Actuators B: Chemical, vol. 165, pp. 44-47 2012.

Ma, et al., Size-Controlled Dissolution of Organic-Coated Silver Nanoparticles, ACS Publications, American Chemical Society, Environmental Science & Technology, vol. 46, pp. 752-759 2012.

Lowry, et al., Long-Term Transformation and Fate of Manufactured Ag Nanoparticles in a Simulated Large Scale Freshwater Emergent Wetland, ACS Publications, American Chemical Society, Environmental Science & Technology, vol. 46, pp. 7027-7036 2012.

Mitrano, et al., Silver nanoparticle characterization using single particle ICP-MS (SP-ICP-MS) and asymmetrical flow field flow fractionation ICP-MS (AF4-ICP-MS)†, JAAS, The Royal Society of Chemistry, J. Anal. At. Spectrom., vol. 27, p. 1131 2012.

Martinez-Munoz, et al., Vacuolar and Plasma Membrane Proton Pumps Collaborate to Achieve Cytosolic pH Homeostasis in Yeast*, The American Society for Biochemistry and Molecular Biology, Inc., Journal of Biological Chemistry, vol. 29, pp. 20309-20319 Jul. 18, 2008.

Molleman, et al., Time, pH, and size dependency of silver nanoparticle dissolution: the road to equilibrium†, The Royal Society of Chemistry, Environmental Science Nano, vol. 4, pp. 1314-1327 2017.

Mueller, et al., Exposure Modeling of Engineered Nanoparticles in the Environment, Environmental Science & Technology, vol. 42, pp. 4447-4453 2008.

Ni, et al., Highly sensitive and selective colorimetric detection of glutathione based on Ag [I] ion-3,3',5,5'-tetramethylbenzidine (TMB), Elsevier, ScienceDirect, Biosensors and Bioelectronics, http://dx.doi.org/10.1016/j.bios.2014.07.021, vol. 63, pp. 47-52 2015.

Saran, et al., A Silver DNAzyme, ACS Publications, American Chemical Society, Analytical Chemistry, vol. 88, pp. 4014-4020 2016.

Schaumann, et al., Understanding the fate and biological effects of Ag- and TiO2-nanoparticles in the environment: The quest for advanced analytics and interdisciplinary concepts, Elsevier, Science of the Total Environment, vol. 535, pp. 3-19, http://dx.doi.org/10.1016/j.scitotenv.2014.10.035 2015.

Shao, et al., Intra- and Intercellular Silver Nanoparticle Translocation and Transformation in Oyster Gill Filaments: Coupling Nanoscale Secondary Ion Mass Spectrometry and Dual Stable Isotope Tracing Study, ACS Publications, American Chemical Society, Environmental Science & Technology, vol. 55, pp. 433-446 2021.

Tuoriniemi, et al., Size Discrimination and Detection Capabilities of Single-Particle ICPMS for Environmental Analysis of Silver Nanoparticles, ACS Publications, American Chemical Society, Analytical Chemistry, vol. 84, pp. 3965-3972 2012.

Sun, et al., Adenine deficient yeast: A fluorescent biosensor for the detection of Labile Zn(II) in aqueous solution, Elsevier, Biosensors and Bioelectrics, vol. 179, pp. 113075 2021.

Yan, et al., In Vivo Bioimaging of Silver Nanoparticle Dissolution in the Gut Environment of Zooplankton, ACS Publications, American Chemical Society, ACS Nano, vol. 12, pp. 12212-12223 2018.

Yan, et al., Real-time monitoring of the dissolution kinetics of silver nanoparticles and nanowires in aquatic environments using an aggregation-induced emission fluorogen†, The Royal Society of Chemistry, ChemComm, vol. 54, pp. 4585-4588 2018.

Yan, et al., Intracellular trafficking of silver nanoparticles and silver ions determined their specific mitotoxicity to the zebrafish cell line†, Royal Society of Chemistry, Environmental Science Nano, vol. 8, pp. 1364-1375 2021.

Yang, et al., Mechanism of Silver Nanoparticle Toxicity Is Dependent on Dissolved Silver and Surface Coating in Caenorhabditis elegans, ACS Publications, American Chemical Society, Environmental Science & Technology, vol. 46, pp. 1119-1127 2011.

Zhang, et al., A signal-on electrochemical biosensor for sensitive detection of silver ion based on alkanethiol-carbon nanotube-oligonucleotide modified electrodes, Elsevier, Sensors and Actuators B: Chemical, vol. 202, pp. 1058-1064 2014.

Hendren, et al., Modeling nanomaterial fate in wastewater treatment: Monte Carlo simulation of silver nanoparticles (nano-Ag), Elsiever, Science of the Total Environment, vol. 449, pp. 418-425 2013.

\* cited by examiner

METHODS FOR DETECTION OF SILVER NANOPARTICLES

TECHNICAL FIELD

The present invention is concerned with a method for detection of intracellularly dissolved silver ions and/or silver nanoparticles in a specimen. The present invention is also concerned with a method for determining the presence and/or size of silver nanoparticles in specimen. The present invention is further concerned with a kit for detection of intracellularly dissolved silver ions and/or silver nanoparticles in a specimen, and/or determining the presence and/or size of silver nanoparticles in specimen.

BACKGROUND OF THE INVENTION

Due to its excellent anti-microbial property, silver (Ag) is the most promising element used in products such as textiles, cosmetics, supplements, cleaning agents, plastics and paints (Benn and Westerhoff, 2008; Mueller and Nowack, 2008). Each year, around 2600 tons of Ag have been used, and the annual worldwide production of nano-Ag was predicted to be 500 tons (Mueller and Nowack, 2008). The simulated concentrations of Ag nanoparticles (AgNPs) were about 1-15% of the total Ag in the environment (Blaser et al., 2008). Pathways of AgNPs entering the aquatic environment include the discharges of wastewaters from sewage treatment plants, terrestrial application of biosolids, and erosion from terrestrial soils to sediments (Lowry et al., 2012). During long-term aging in the environment, many factors such as location, biotic/abiotic transformation and dissolution could influence the distribution, persistence, bioavailability and toxicity of AgNPs (Choi et al., 2009; Hendren et al., 2013; Yan et al., 2021). Although the toxicity of AgNPs was mainly related to their dissolution to $Ag^+$ and the risk quotient (ratio of the predicted environmental concentration to the predicted no effect concentration) of AgNPs was less than 1 (Mueller and Nowack, 2008; Yan et al., 2018a), the bioaccumulation of AgNPs could enhance the available Ag to organisms. Thus, the detection and quantifying the bioavailable AgNPs and cellular dissolved $Ag^+$ are critical in the assessments of environmental risks of AgNPs.

Detection of silver ions or silver particles has been around. One purpose of seeking to detect presence of silver ions or nanoparticles is, for example, to ascertain whether there are such silver nanoparticles and/or how much in a specimen or environment sample. However, different conventional methodologies have different limitations. For example, some conventional methodologies are not able to detect silver ions as a result of intracellular dissolution to silver ions. Other conventional methodologies are not able to detect silver nanoparticles of a particular size range. Further, some methodologies are too complicated to be commercially realistic.

The present invention seeks to address at least the above, and/or to provide a useful alternative to the public.

SUMMARY OF THE INVENTION

According to a first aspect of the present invention, there is provided a method for detection of presence and/or quantities of silver nanoparticles in a specimen, comprising the steps of a) providing a detection organism suspended in a medium, said organism is a yeast adapted to autofluoresce in the presence of zinc ions and de-fluoresce in the presence of silver ions, b) treating the detection organism with zinc ions thus effecting autofluorescence therefrom, and then measuring degree of fluorescence of the detection organism suspended medium, c) adding the specimen to the detection organism suspended medium, treating the detection organism therein with the specimen for a period of time, and measuring change of fluorescence of the detection organism-suspended medium over time, d) calculating amount of silver ions intracellularly dissolved from the silver nanoparticles and accumulated in the detection organism in view of the change of fluorescence, and e) extrapolating quantity of silver nanoparticles in the specimen in view of the change of fluorescence and the amount of the intracellularly dissolved silver ions.

Preferably, the detection organism may be an adenine deficient yeast. More preferably, the adenine deficient yeast may be *Saccharomyces cerevisiae*.

In an embodiment, the concentration of the intracellularly dissolved silver ions may correlate to the concentration of the silver nanoparticles in the specimen.

In one embodiment, the method may be configured to detect silver nanoparticles with a size ranging from 4.5-9 nm, or an average size of 7 nm, in diameter. In a more specific embodiment, the method may be configured to detect silver nanoparticles with a concentration as low as 8.9 µg/L.

In another embodiment, the biomass of the adenine deficient yeast indicative of the concentration thereof in the detection organism suspended medium may range from $OD_{600}$=0.005 to $OD_{600}$=0.02. In a specific embodiment, the biomass of the adenine deficient yeast may be $OD_{600}$=0.005.

Advantageously, in the treating the detection organism with zinc ions, the method may comprise a step of optimizing the concentration of the zinc ions in the detection organism-suspended medium to 0.025-0.1 µM for at least 1 hour. The concentration of the zinc ions in the detection organism-suspended medium may preferably be optimized to 0.05 µM.

Suitably, the time period of the detection organism being treated with the specimen may be 30-60 mins, and wherein measurement of the change in fluorescence is taken duration and after the time period. In a specific embodiment, the time period may be 30 mins.

According to a second aspect of the present invention, there is provided a method for screening for silver nanoparticles with a diameter of 4.5-9 nm or an average diameter of 7 nm in a specimen from larger silver nanoparticles, comprising a) providing a detection organism suspended in a medium, said organism is a yeast adapted to autofluoresce in the presence of zinc ions and de-fluoresce in the presence of silver ions, b) treating the detection organism in detection organism suspended medium with zinc ions thus effecting autofluorescence thereof, and then measuring degree of fluorescence of the detection organism-suspended medium, c) adding the specimen to the detection organism suspended medium and treating the detection organism therein with the specimen for a period of time, and then measuring change of fluorescence of the detection organism-suspended medium over time, the change in fluorescence is indicative of amount of silver ions dissolved from the silver nanoparticles, and d) determining the presence of silver nanoparticles with a diameter of 4.5-9 nm or an average diameter of 7 nm in the specimen by examining for any response in fluorescence in that a positive response is indicative of presence of silver nanoparticles with a diameter of 4.5-9 nm or an average diameter of 7 nm in the specimen.

Preferably, the larger silver nanoparticles may have a diameter of 16-26 nm or an average diameter of 20 nm.

In a preferred embodiment, the detection organism may be adenine deficient yeast. Specifically, the adenine deficient yeast may be *Saccharomyces cerevisiae*.

BRIEF DESCRIPTION OF DRAWINGS

Some embodiments of the present invention will now be explained, with reference to the accompanied drawings, in which.

DETAILED DESCRIPTION OF PREFERRED EMBOPDIMENTS OF THE INVENTION

Figure 1:
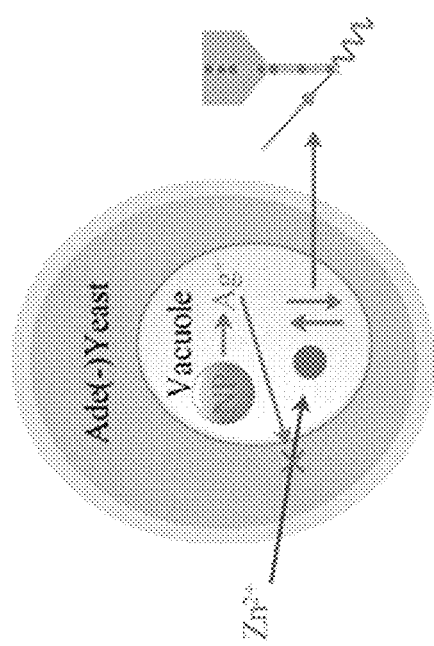
FIG. 1 is a schematic diagram showing the interaction between an Ade(-) yeast cell, Zn ions ($Zn^+$) and Ag ions.

Due to its excellent anti-microbial property, Ag is the most promising element used in products such as textiles, cosmetics, supplements, cleaning agents, plastics and paints (Benn and Westerhoff, 2008; Mueller and Nowack, 2008). Each year, around 2600 tons of Ag have been used, and the annual worldwide production of nano-Ag was predicted to be 500 tons (Mueller and Nowack, 2008). The simulated concentrations of Ag nanoparticles (AgNPs) were about 1-15% of the total Ag in the environment (Blaser et al., 2008). Pathways of AgNPs entering the aquatic environment include the discharges of wastewaters from sewage treatment plants, terrestrial application of biosolids, and erosion from terrestrial soils to sediments (Lowry et al., 2012). During long-term aging in the environment, many factors such as location, biotic/abiotic transformation and dissolution could influence the distribution, persistence, bioavailability and toxicity of AgNPs (Choi et al., 2009; Hendren et al., 2013; Yan et al., 2021). Although the toxicity of AgNPs was mainly related to their dissolution to $Ag^+$ and the risk quotient (ratio of the predicted environmental concentration to the predicted no effect concentration) of AgNPs was less than 1 (Mueller and Nowack, 2008; Yan et al., 2018a), the bioaccumulation of AgNPs could enhance the available Ag to organisms. Thus, quantifying the bioavailable AgNPs and cellular dissolved $Ag^+$ are critical in the assessments of environmental risks of AgNPs.

The most direct method to determine AgNPs is to distinguish AgNPs from the background dissolved Ag (Schaumann et al., 2015). Ultracentrifugation and ultrafiltration methods have been widely applied in the differentiation of these two forms (AgNPs versus $Ag^+$), but such methods are limited by the nonspecific adsorption and excessive treatment duration, which induce further dissolution of AgNPs and confound the measurement of dissolution dynamics (Fabricius et al., 2014). Cloud point extraction was also used to differentiate AgNPs and $Ag^+$, but the detected value of $Ag^+$ was higher than that typically obtained by other methods (Chao et al., 2011). Following the separation of AgNPs and $Ag^+$, the concentrations of Ag were further determined by traditional methods such as the inductively coupled plasma mass spectrometry (ICP-MS), atomic absorption spectrometry, and microparticle-induced X-ray emission. These methods are generally limited by complicated pretreatment and high cost (Sun and Wang, 2021). Based on the principle that particles could be injected slowly into the ICP-MS detector, the single particle ICP-MS (SP-ICP-MS) could sensitively determine both the composition and number concentration of NPs (Tuoriniemi et al., 2012). Although SP-ICP-MS distinguishes AgNPs (as spikes) from the ion background, it is still advisable to remove $Ag^+$ with an ion exchange resin to increase the accuracy, which adds another complicated step to the method (Hadioui et al., 2014). The biggest disadvantage of SP-ICP-MS is its size limitation (approximately 18 nm), making it unable to determine the most toxic AgNPs in the environment (Schaumann et al., 2015).

To evaluate the biological effects of AgNPs, determining the intracellularly dissolved $Ag^+$ from AgNPs is important. Chemosensors such as organic fluorophores could be used to capture the dissolved $Ag^+$. The use of tetrazole-functionalized tetraphenylethylene derivative 1 could determine $Ag^+$ at concentration as low as 30 nM and the fluorescence intensity was not reduced by biomolecules like cysteines (Yan et al., 2018b). Due to the high biocompatibility and hydrophilicity, the fluorophore was successfully used to track the intracellularly dissolved $Ag^+$ in zebrafish cell lines (Yan et al., 2021). Also, coating another fluorophore on the surface of AgNPs enabled the differentiation of intracellularly dissolved $Ag^+$ and AgNPs. However, the complicated synthesis, purification, and narrow effective pH range make the use of organic fluorophore limited, whereas the coated fluorophore also affect the original behavior of AgNPs. More importantly, using these probes requires the involvement of foreign matters which may influence the intracellular dissolution of AgNPs. Nanoscale secondary ion mass spectrometry (NanoSIMS) provided in situ evidence to the subcellular distribution of AgNPs and $Ag^+$, but the cells need to be pretreated (Shao et al., 2020). Studies leading to the present invention indicates that individual biosensors can provide toxicological evidence and give evidence to bioremediation and environmental impact assessment. Besides, since some organisms are able to accumulate the nanoparticles, analogous to bio-collectors. Applications of bio-collectors may lower the detection limit of AgNPs in environment and further predict the likely biological effects of AgNPs.

In the experiments leading to the present invention, an adenine deficient yeast (Ade(−) yeast) acting as a detection organism was cultured to quantify AgNPs by determining the intracellularly dissolved $Ag^+$. The methodology is based on the result that the autofluorescence increase of Ade(−) yeast was enhanced by $Zn^{2+}$ but decreased by $Ag^+$. In essence, Ade(−) yeast acts as a biosystem for the bioaccumulation of ultra-small AgNPs and their intracellular dissolution. The biosystem thus 'collects'/'concentrates' the surrounding AgNPs and can then be used to quantify the extracellular AgNPs thereof. The intracellularly dissolved $Ag^+$ can thus be determined and compared with the total Ag accumulation. This methodology for the first time provides a yeast-based individual biosensor to determine both AgNPs and their intracellularly dissolved $Ag^+$ in aqueous suspension. The method has ultra-high sensitivity, low detection limit, and wide potential in environmental assessment based on biosensors.

The following provides further illustrations of the experiments and discusses the results thereof.

Materials and Methods

Yeast Culture

Wild type *Saccharomyces cerevisiae* (Yeast W303) were inoculated in YPD broth (Sigma) at 180,000 cells/mL and cultured for 24 h (30° C., 200 rpm) to obtain the adenine deficient yeast (Ade(−) yeast). Ade(−) yeast was preserved at 4° C. within 24 h and washed by ultrapure water for 3 times prior to use.

Determination of Fluorescence Intensity by Flow Cytometry

Fluorescence intensity of 10,000 cells was recorded by flow cytometry (BD FACSAria™ III sorter, USA) through FITC channel (Ex/Em 494/519 nm). To obtain the highest sensitivity to $Ag^+$, the concentration of added $Zn^{2+}$, biomass of yeast cells and time to add $Ag^+$ were firstly determined and optimized. Briefly, the biomass of the yeast cell was diluted to different OD values (0.005, 0.01 and 0.02) and $Ag^+$ at 20 nM was added in the medium for 1 h, followed by the addition of $Zn^{2+}$ at 0.1/0.05/0.025 µM for another 1 h. In particular, $Ag^+$ at 20 nM was added at different time points (60/45/30/15/0 min before the addition of 0.05 µM-$Zn^{2+}$ or 60 min after the addition of $Zn^{2+}$). The fluorescence decrease (%) after $Ag^+$ addition was calculated as: (fluorescence intensity in the control group-fluorescence intensity in the test group)/fluorescence intensity in the control group× 100%. The fluorescence intensity of Ade(−) yeast cells cultured with $Zn^{2+}$ was recorded as the control, while that of yeast cultured with $Ag^+$ and $Zn^{2+}$ was recorded as the test group.

Quantification of $Ag^+$ in the Medium and Commercial Product

To obtain the highest sensitivity to $Ag^+$ and facilitate the direct determination by flow cytometry, the biomass of the Ade(−) yeast was diluted to be 0.005. Cells (OD value=0.005) were added in 2.5 g/L glucose-based medium (containing $Ag^+$ at 0/5/10/15/20 nM) and pre-cultured for 1 h. After that, $Zn^{2+}$ at 0.05 µM was added in the medium, followed by the detection of fluorescence intensity by flow cytometry after 1 h. The relationship between [$Ag^+$] and fluorescence decrease was thus obtained. Influence of $Ag^+$ on autofluorescence of yeast cells was determined by culturing the yeast in medium only containing $Ag^+$ for 2 h and the fluorescence change was determined by flow cytometry. To quantify the total Zn/Ag contents, Ade(−) yeast cells (OD value=0.005) were cultured as described above, washed with ultrapure water for 3 times, digested with 1 mL 69% nitric acid (trace metal grade) and analyzed using ICP-MS (NexION 300X, Perkin Elmer, USA). The accumulated Zn or Ag was quantified as µg Zn/µg P or µg Ag/µg P, where P represented the phosphorus content in the yeast. Accumulation of Ag in the first hour of incubation was analyzed.

Before the practical application, the interference of other metals on the sensitivity to $Ag^+$ was determined. Ade(−) yeast cells were firstly cultured in 2.5 g/L glucose containing $Ag^+$ (20 nM) for 1 h, followed by transferring the cells to the medium with different metals (Al, As, Ca, Cd, Co, Cr, Cu, Fe, Mg, Mn, Ni, Pb, Se, Ti, Hg at 20 nM) and 0.05 µM $Zn^{2+}$. Acidic solution ($HNO_3$, pH=3.00) was neutralized to pH=7.00 using NaOH, followed by the addition of 20 nM $Ag^+$ and 0.05 µM $Zn^{2+}$, yeast culture and detection by flow cytometry. The commercial product used in this test was SILVER IONS DROPS distributed by Real Pleasure Ltd. Cells (OD value=0.005) were put in 2.5 g/L glucose-based medium (containing $Ag^+$ at 0/10/15/20/25/30/35 nM or SILVER IONS DROPS 0.5%6) and pre-cultured for 1 h. After that, $Zn^{2+}$ (0.05 µM) was added in the medium, followed by the detection of fluorescence intensity by flow cytometry after 1 h. Cells cultured with $Ag^+$ and $Zn^{2+}$ were washed with ultrapure water for 3 times, digested with 1 mL 69% nitric acid (trace metal grade) and analyzed using ICP-MS (NexION 300X, Perkin Elmer, USA).

Synthesis and Characterization of AgNPs

AgNPs of two different sizes (7 nm and 20 nm) were synthesized. The 7 nm citrate-coated AgNPs were synthesized by pipetting NaBH$_4$ (120 μL at 100 mM) to reduce AgNO$_3$ (100 μL at 100 mM), with 40 mL of trisodium citrate dihydrate (1.25 mM) added. After stirring for 3 h, the synthesized 7 nm citrate-coated AgNPs were collected, washed by ultrapure water and stored in dark (4° C.). The 20 nm citrate-coated AgNPs were synthesized by injecting citrate (2 mL at 34 mM) to boiling AgNO$_3$ (100 mL at 1 mM) under stirring and the reaction lasted for 3 h, followed by collection, washing and storage in dark (4° C.). Morphology of the synthesized AgNPs was observed by a transmission electron microscopy (TEM, JEM 2010). Dissolution of AgNPs at 10/25/50/75 μg/L was determined using ICP-MS coupled with ultrafiltration (10000 kDa, 3000 g, 5 min, VIVASCIENCE, USA).

Quantification of AgNPs Using Adenine Deficient Yeast and Intracellular Dissolution To remove the influence of extracellularly dissolved Ag$^+$, cysteine (0.5 μM) was added in the 2.5 g/L glucose-based medium, followed by the addition of AgNPs at 10/25/50/75 μg/L. AgNPs (7 nm) and AgNPs (20 nm) were mixed to obtain the solvent containing the total Ag at 100 μg/L (Ag as nanoform): 100% 20-Ag+0% 7-Ag, 75% 20-Ag+25% 7-Ag, 62.5% 20-Ag+37.5% 7-Ag, 37.5% 20-Ag+62.5% 7-Ag, 25% 20-Ag+75% 7-Ag, 0% 20-Ag+100% 7-Ag. After 1 h preculturing time, yeast cells were washed for 3 times and cultured in glucose medium for 1 h to facilitate the intracellular dissolution of AgNPs. After that, Zn$^{2+}$ (0.05 μM) was added in the medium, followed by the detection of fluorescence by flow cytometry after 1 h. Total accumulation of Ag in AgNPs treated yeast cells was determined by collecting the yeast cells after 1 h/3 h for ICP-MS analysis.

After preculturing in 2.5 g/L glucose medium (containing 0.5 μM cysteine and AgNPs at 75 μg/L) for 1 h, yeast cells were washed and cultured with cysteine for another 2 h. Flow cytometry was used to determine the change of fluorescence and thus the fluorescence change caused by AgNPs was determined. ICP-MS was used to determine the intracellular accumulation of Ag. Based on the relationship between fluorescence decrease and accumulated Ag, the intracellular Ag$^+$ dissolved from AgNPs was determined. HNO$_3$ (1 M) was used to adjust the pH value of ultrapure water to 5.20, and AgNPs at 75 μg/L were added in the medium for 3 h, followed by ultrafiltration (3000 g for 5 min) and detection of dissolved Ag$^+$ by ICP-MS. Dissolution rate of Ag NP was recorded as: [Ag$^+$]/[AgNPs in 75 μg/L Ag NP]*100%.

Statistical Analysis

Data were expressed as the mean±standard deviation and performed in triplicate. Statistical significance was determined using one-way analysis of variance and compared using LSD's test in SPSS 22.0.

Results and Discussion

Optimization of the Method to Detect Intracellular Ag$^+$

Figure 2:
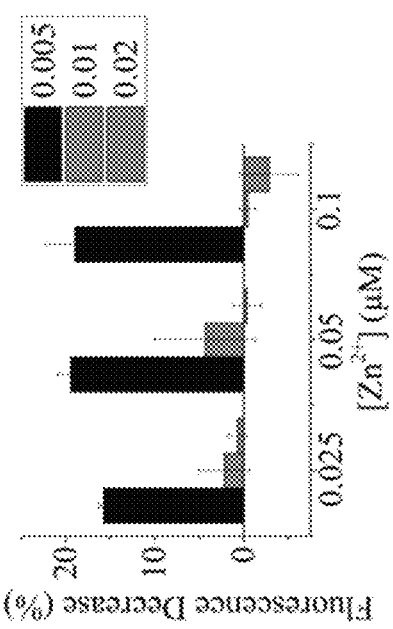
FIG. 2 is a graph showing the optimization of biomass and added $Zn^{2+}$.
Figure 3:
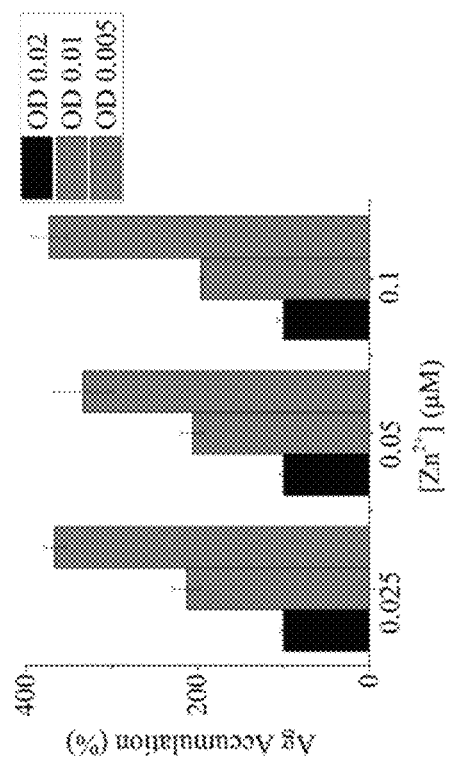
FIG. 3 is a graph showing a change of accumulated Ag in yeast with different biomass and $Zn^{2+}$ addition.
Figure 4:
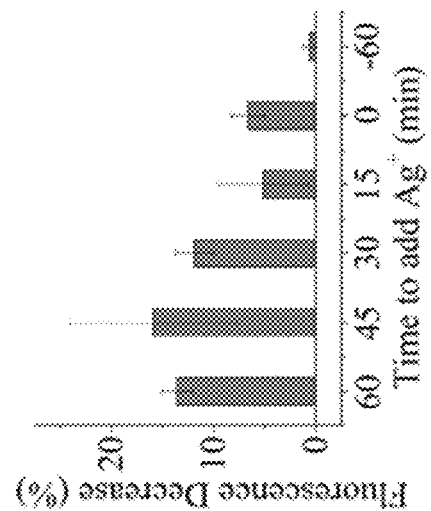
FIG. 4 is a graph showing the optimization time for to adding $Ag^+$.

AgNPs internalized by cells were transformed to ionic Ag in acidic organelles, and the intracellularly dissolved Ag$^+$ induces cytotoxicity, thus yielding to the detection tool used in the present invention. Based on this Ag$^+$ directed fluorescence decrease, the concentration of intracellular Ag$^+$ dissolved from AgNPs was indirectly determined by monitoring the fluorescence change of yeast in the presence of Zn$^{2+}$, as shown in FIG. 1. Thus, a method to optimize the highest sensitivity to intracellular Ag$^+$ was sought. FIG. 2 is a graph indicating that low biomass (OD=0.005) led to a higher sensitivity to Ag$^+$ and the increased sensitivity to Ag$^+$ was due to the high accumulation of Ag in cells (nearly 4 folds higher than high biomass group, see FIG. 3), thus the biomass was optimized to be 0.005 (OD value) to accumulate AgNPs. The amount of added Zn$^{2+}$ did not induce significant change of Ag accumulation (please also see FIG. 3), but Zn$^{2+}$ at a higher concentration resulted in slightly higher sensitivity to Ag$^+$ (please see FIG. 2). The added [Zn$^{2+}$] was thus optimized to be 0.05 μM to obtain the highest sensitivity. Previous studies show that the metal uptake efficiency of yeast cells was dependent on the species of metals, thus the efficient utilization of Zn$^{2+}$ might inhibit the negative effects caused by Ag$^+$ if these two ions existed simultaneously. FIG. 4 is a graph showing that the highest sensitivity was obtained when Ag$^+$ was added at least 30 min before adding Zn$^{2+}$. Therefore, the intracellular Ag$^+$ should remain in the cells for over 30 min prior to the addition of Zn$^{2+}$, providing sufficient time for intracellular Ag$^+$ to take effect.

Figure 5:
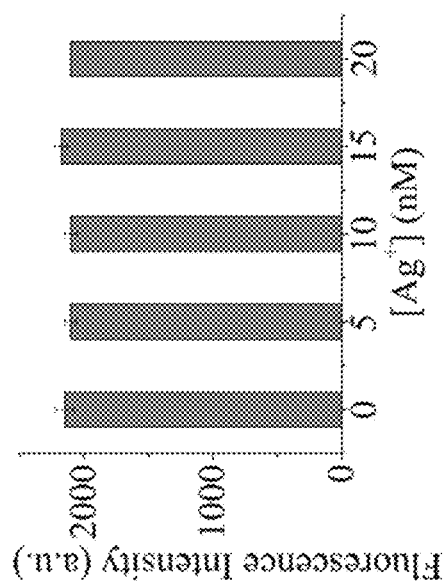
FIG. 5 is a graph showing a change in fluorescence caused by $Ag^+$.
Figure 6:
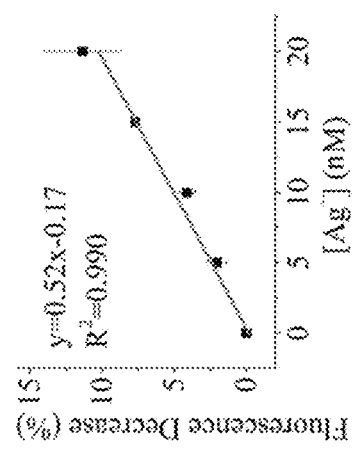
FIG. 6 is a graph showing the relationship between concentration of $Ag^+$ and fluorescence decrease of Ade(-) yeast.
Figure 7:
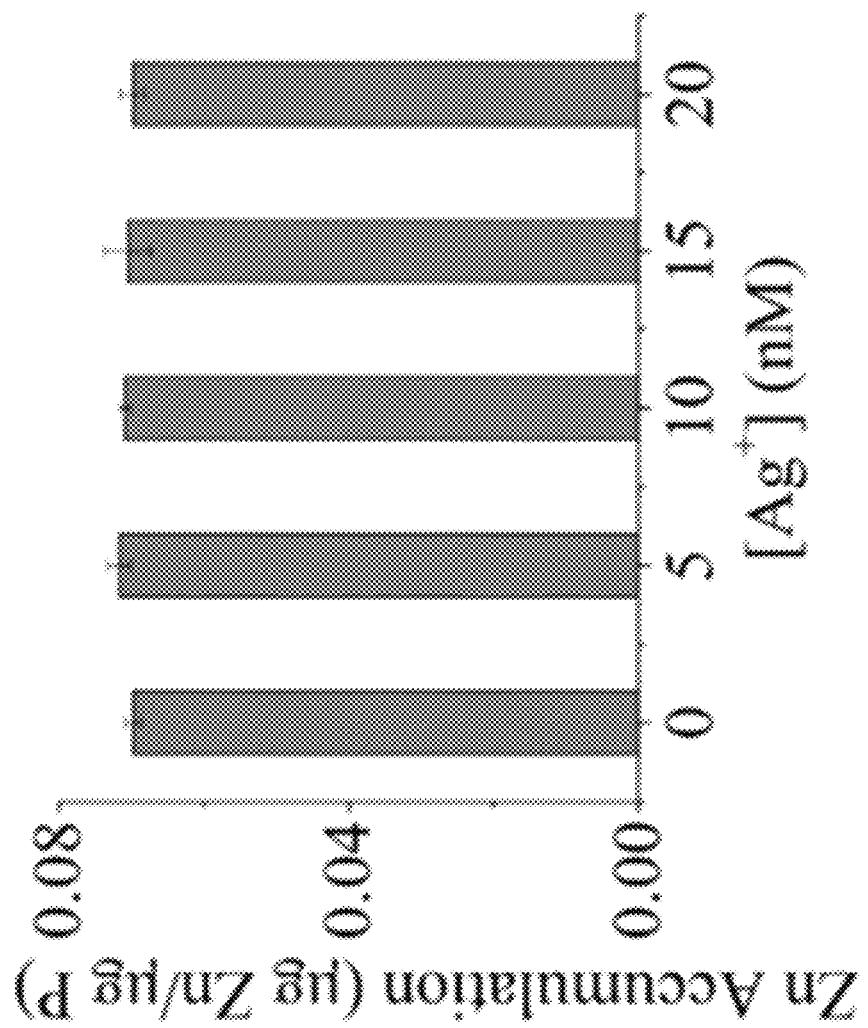
FIG. 7 is a graph showing the accumulation of Zn with different $[Ag^+]$ addition.
Figure 8:
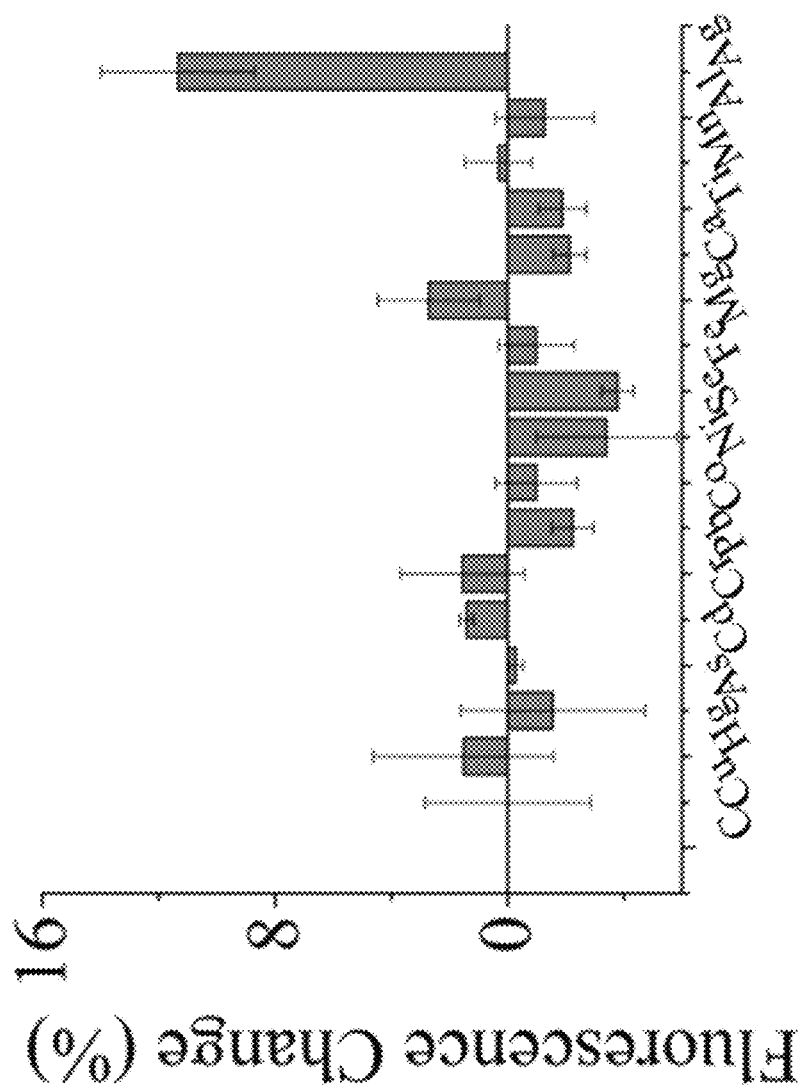
FIG. 8 is a graph showing the interference effects of other metal ions.
Figure 9:
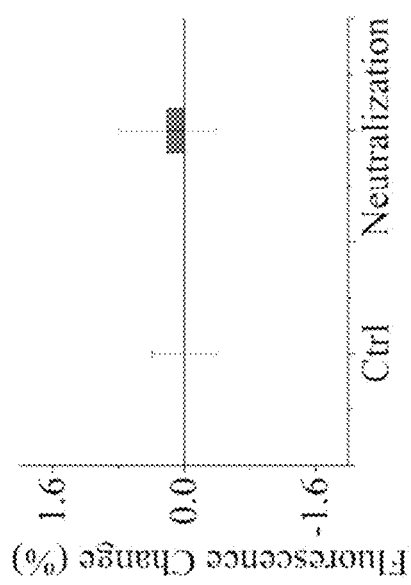
FIG. 9 is a graph showing the influence of pH change after neutralization.
Figure 10:
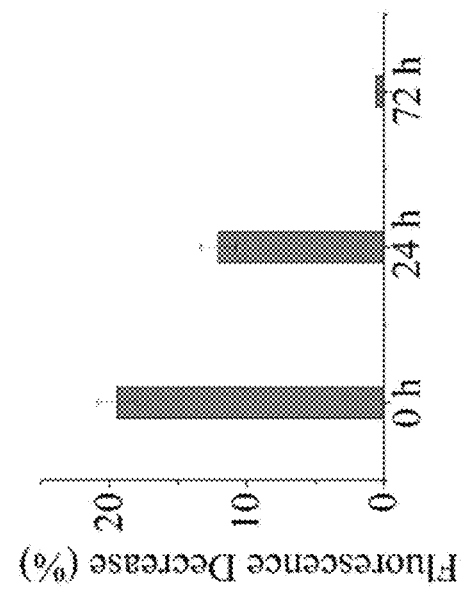
FIG. 10 is a graph showing stability of the detection performance.

Although no fluorescence decrease was induced by Ag$^+$ at 5-20 nM without adding Zn$^{2+}$ (FIG. 5), the biosystem became more sensitive in the presence of Zn$^{2+}$ and determined Ag$^+$ at 5 nM ($R^2$=0.990, FIG. 6). This value was much lower than the detection limit of many organic probes or enzyme-based biosensor at 20-50 nM (Liu et al., 2012; Ni et al., 2015; Saran and Liu, 2016). The results from these experiments showed that the accumulation of intracellular Ag$^+$ correlated well with the fluorescence decrease ($R^2$=0.993, FIG. 6), and the lowest concentration of the accumulated Ag$^+$ that can be determined by Ade(−) yeast was as low as 3.77 ng Ag/pg P (according to 5 nM added Ag). This value (3.77 ng Ag/pg P) was also the lowest detectable Ag$^+$ dissolved from the internalized AgNPs. The unchanged accumulation of Zn in the presence of different amounts of accumulated Ag$^+$ further indicated that the fluorescence decrease caused by Ag$^+$ was totally owing to the side effect of intracellular Ag$^+$, with no influence on Zn uptake (FIG. 7). Due to the biological activity facilitated detection of Ag$^+$, the individual biosensor could provide more toxicological evidence and environmental safety assessment of both Ag$^+$ and AgNPs, although some electrochemical biosensors were designed to obtain higher sensitivity to Ag (e.g. 2 nM). Reference is also made to Zhang and Yan, 2014. These results indicate that the presence of the intracellular silver ions can be detected with this methodology FIG. 8 shows that no significant effect on Ag$^+$ directed fluorescence decrease was induced by other metals at 20 nM, indicating the high selectivity of this biosensor to Ag$^+$. Studies leading to the present invention suggests that strong binding of Ag$^+$ on thiols results in the highest sensitivity of yeast to Ag$^+$ among all metals. Although ultralow or ultrahigh pH values would influence the effectiveness of Ade(−) yeast, the neutralized sample caused no side effects on the detection (please see FIG. 9). FIG. 10 shows that the sensitivity of Ade(−) yeast to Ag$^+$ decreased as the storage time of yeast increased, indicating that the cultured yeast cells was effective only within 24 h. Therefore, both yeast cells and the standard curve used for quantification of AgNPs should be freshly prepared before use.

Figure 11:
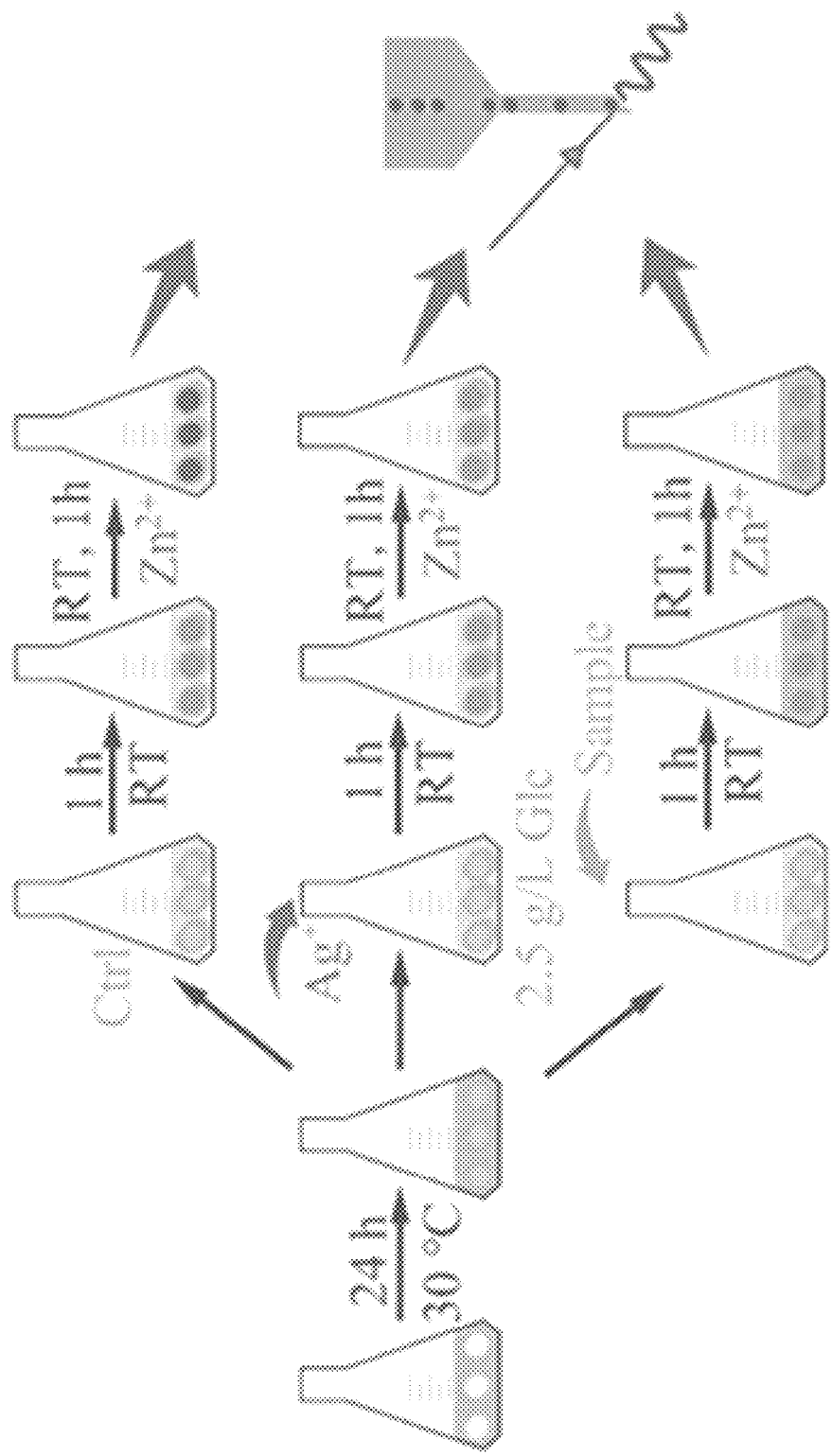
FIG. 11 is a diagram showing an optimized method to determine dissolved $Ag^+$.
Figure 12:
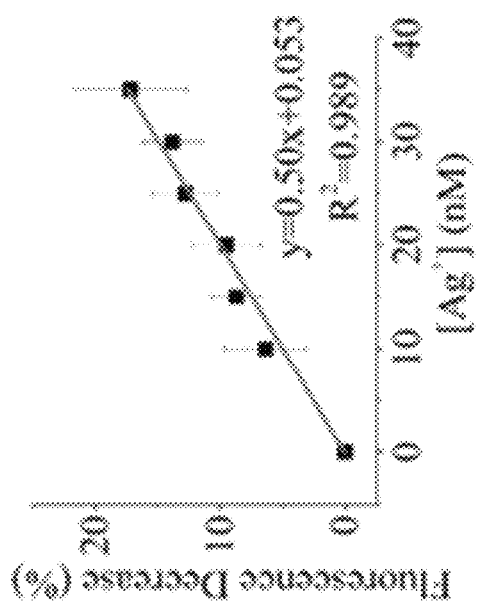
FIG. 12 is a graph showing the relationship between concentration of $Ag^+$ and fluorescence decrease of Ade(-) yeast.
Figure 13:
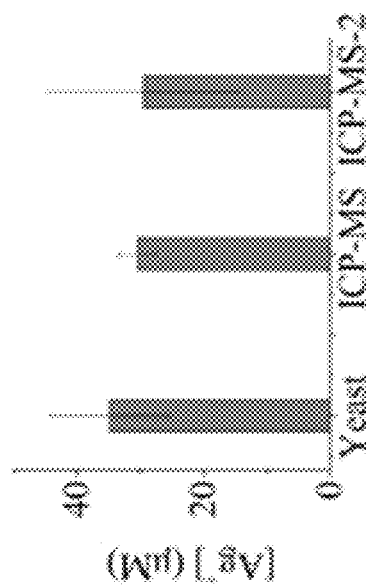
FIG. 13 is a graph showing the concentration of $Ag^+$ in ear drops.
Figure 14:
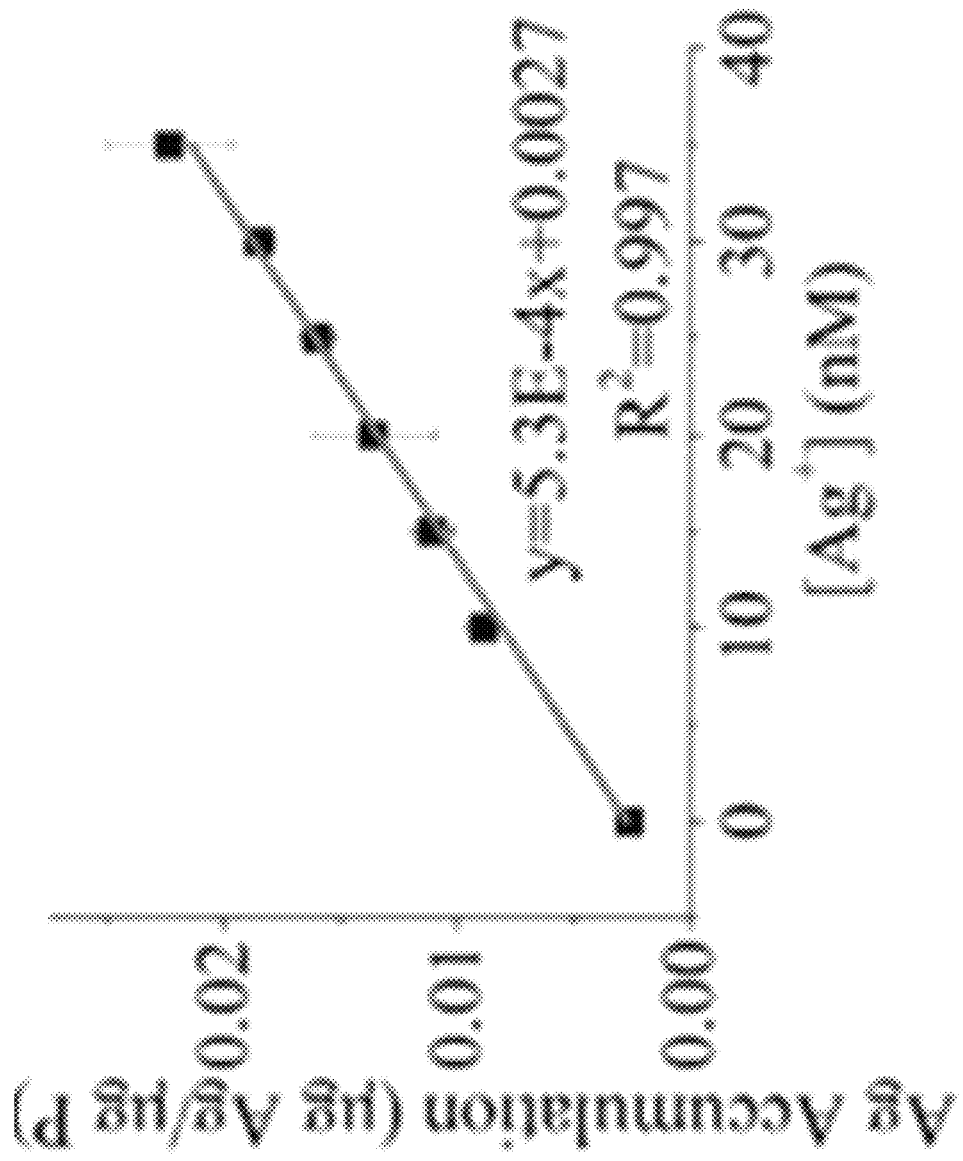
FIG. 14 is a graph showing the relationship between concentration of $Ag^+$ and total Ag accumulation.

To further verify the effectiveness of this biosystem of the present invention to determine the intracellular Ag$^+$, one Ag containing commercial product (ear drop) was diluted in the extracellular medium and thus performance in the presence of other interference factors could be identified. Based on the abovementioned optimization, the method was as follows (FIG. 11): 1. Obtain of Ade(−) yeast; 2. Coculturing Ade(−) yeast with sample containing Ag$^+$ for 1 h; 3. Addition of Zn$^{2+}$ at 0.05 μM for 1 h; 4. Detection of the fluorescence intensity by flow cytometry. Based on the relationship between [Ag$^+$] and fluorescence decrease ($R^2$=0.989, FIG. 12), [$Ag^+$] in ear drops was quantified to be 34.8±9.4 µM (FIG. 13). Using ICP-MS, contents of Ag accumulated in yeast cells were determined and [$Ag^+$] in ear drops was quantified (29.5±15.2 µM) based on the relationship between [$Ag^+$] and Ag accumulation ($R^2$=0.997, FIG. 14). The [$Ag^+$] in ear drops determined directly by ICP-MS was 30.4±3.0 µM. Results obtained by these 3 methods were comparable (FIG. 13), indicating the effectiveness of using Ade(−) yeast to determine [$Ag^+$] in the commercial product on the basis of the fluorescence decrease caused by bioaccumulation of Ag and interferents caused few effects on the detection. Overall, the above data indicates that Ade(−) yeast is one model organism which can be used as a detection organism for detecting $Ag^+$ in a complicated medium, including quantifying the bioavailable AgNPs and monitoring the transformation of AgNPs to ionic Ag intracellularly.

Quantification of AgNPs Based on Bioaccumulation and Intracellular Dissolution

Figure 15:
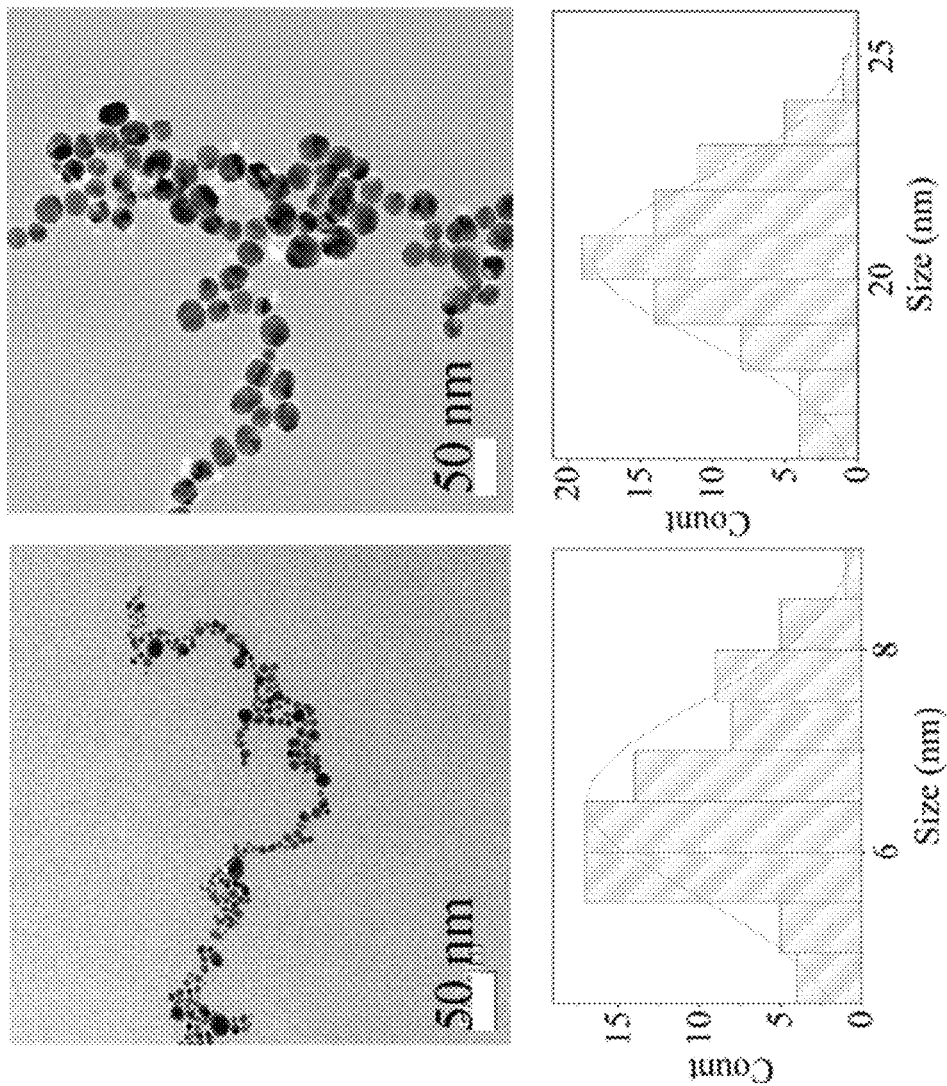
FIG. 15 are photographic images and graphs showing the morphology and size distribution of AgNPs.
Figure 16:
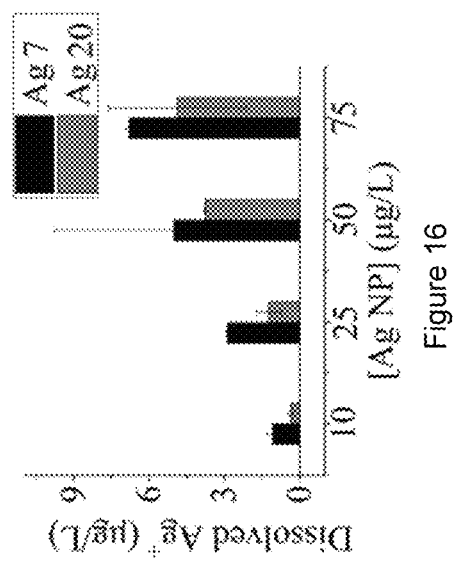
FIG. 16 is a graph showing extracellularly dissolved $Ag^+$ from AgNPs.
Figure 17:
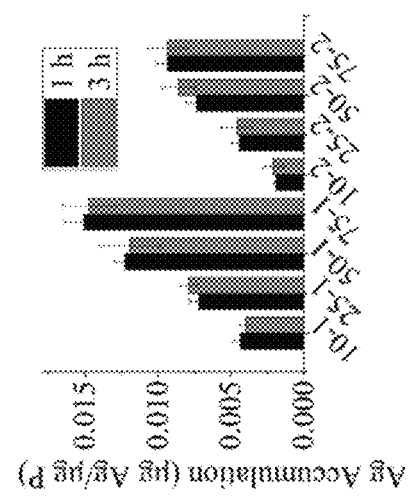
FIG. 17 is a graph showing bioaccumulated Ag in Ade(-) yeast.
Figure 18:
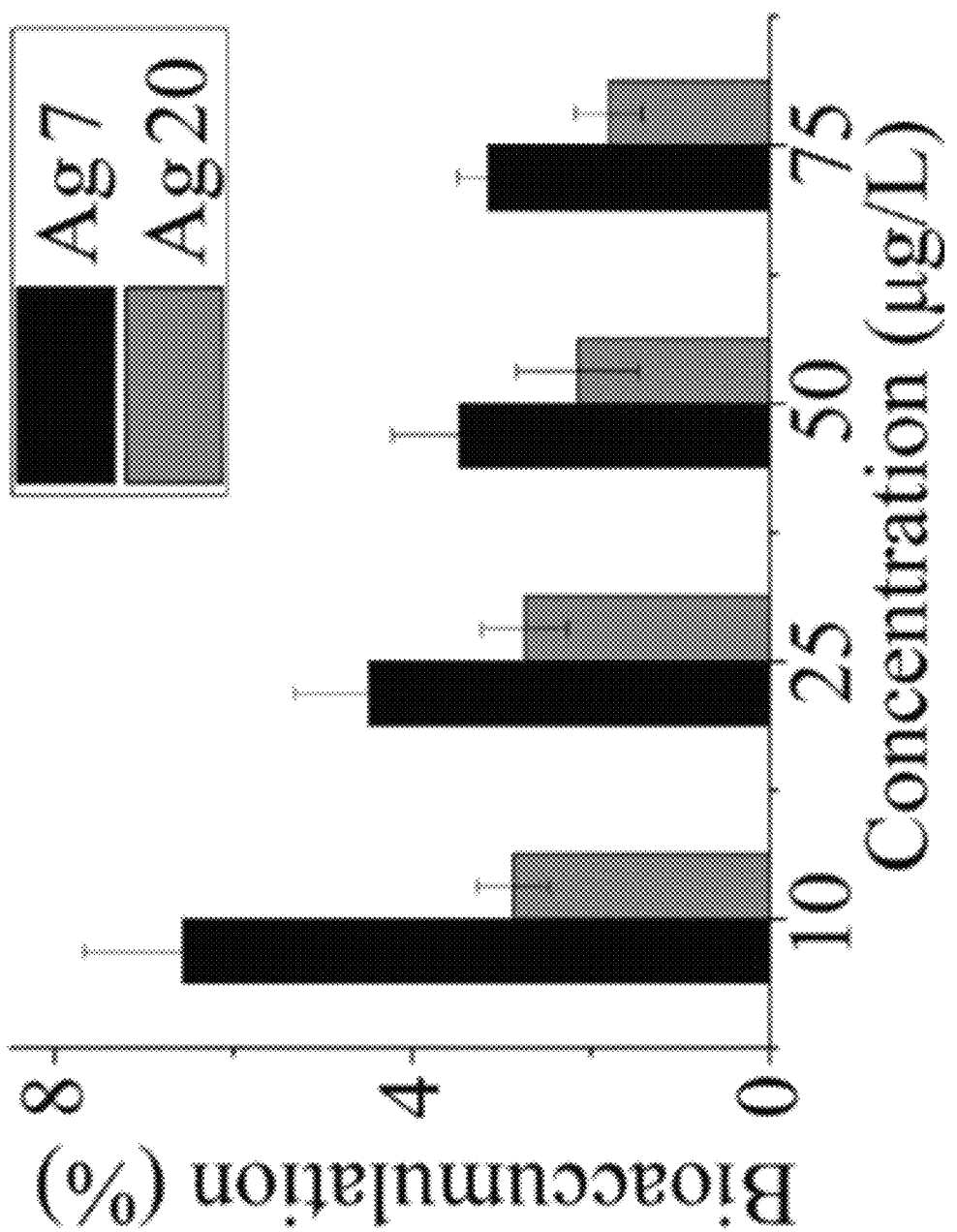
FIG. 18 is a graph showing bioaccumulation rate of AgNPs.

AgNPs of 7 nm and 20 nm sizes were synthesized in this study (FIG. 15). The dissolution ability of 7 nm AgNPs was higher than that of 20 nm ones, as shown by the higher concentration of dissolved $Ag^+$ from the smaller sized NPs (FIG. 16). Based on the extracellular dissolution of these AgNPs, the real concentration of AgNPs (calculated as: total Ag-dissolved $Ag^+$) could thus be determined as: 8.9 in 10 µg/L, 22.1 in 25 µg/L, 45.0 in 50 µg/L and 68.2 in 75 µg/L for 7 nm AgNPs; 9.7 in 10 µg/L, 23.8 in 25 µg/L, 46.2 in 50 µg/L and 70.1 in 75 µg/L for 20 nm AgNPs, respectively. Whereas less 7 nm AgNPs were exposed to Ade(−) yeast compared with the 20 nm AgNPs, they displayed a higher bioaccumulation (FIG. 17). The cell wall of some cells in some microorganism is the first barrier to inhibit the cellular uptake of AgNPs for some microorganisms. Experiments leading to the present invention has shown that around 3-8% of the 7 nm AgNPs was accumulated within 1 h, in contrast to <3% of 20 nm AgNPs (FIG. 18).

Figure 19:
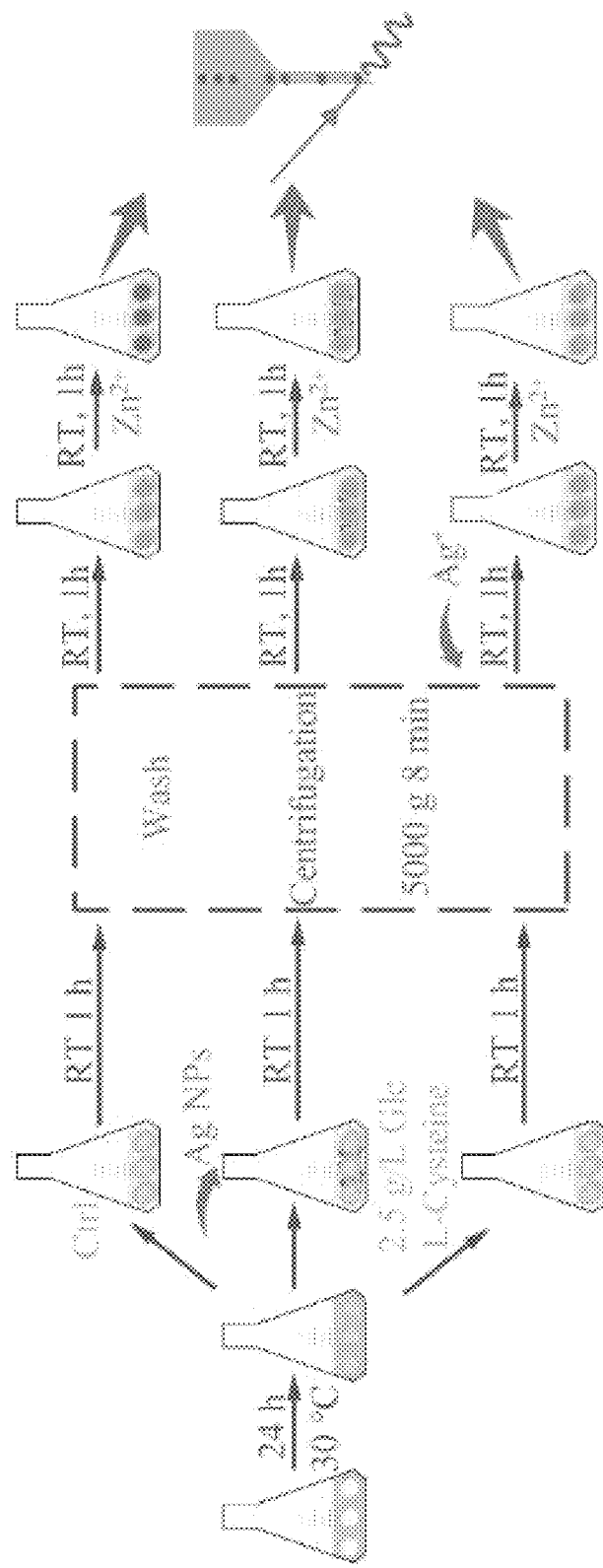
FIG. 19 is a schematic diagram showing an optimized method to determine AgNPs.
Figure 20:
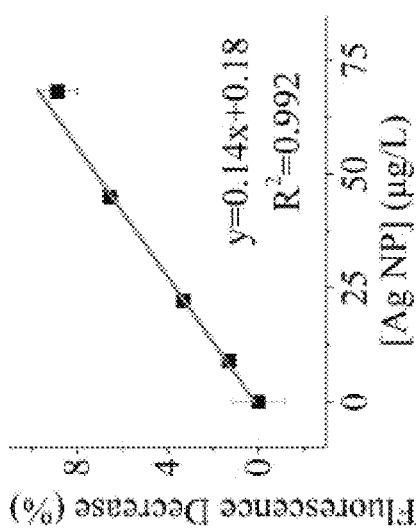
FIG. 20 is a graph showing the relationship between concentration of Ag-7 and fluorescence decrease of Ade(-) yeast.
Figure 21:
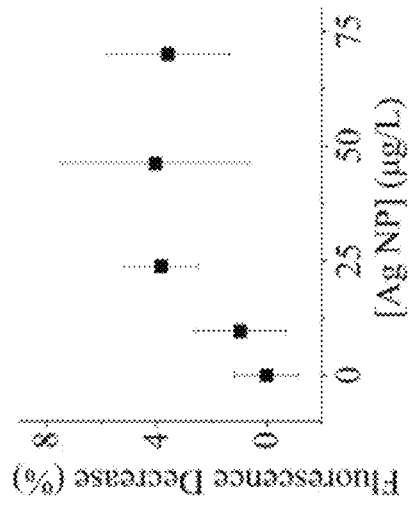
FIG. 21 is a graph showing the relationship between concentration of Ag-20 and fluorescence decrease of Ade(-) yeast.
Figure 22:
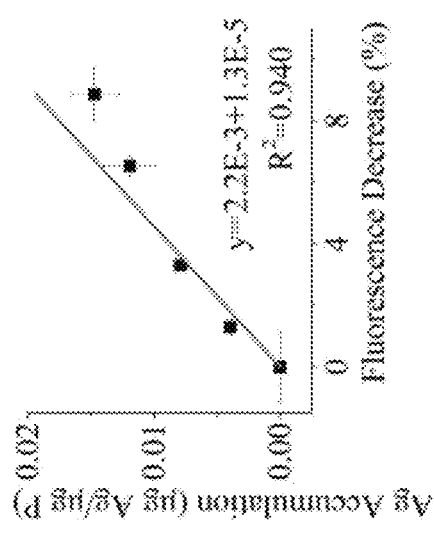
FIG. 22 is a graph showing the relationship between fluorescence decrease and accumulation of Ag-7.
Figure 23:
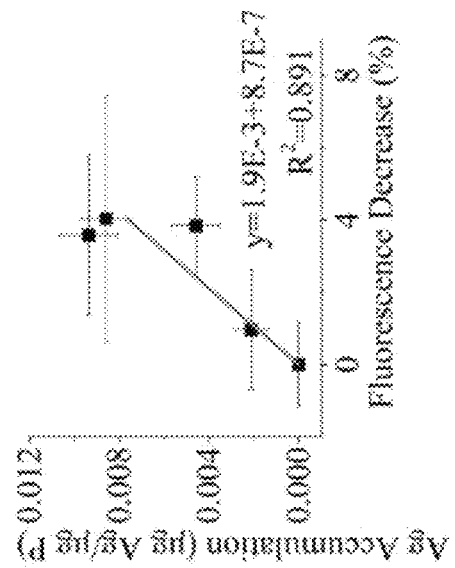
FIG. 23 is a graph showing the relationship between fluorescence decrease and accumulation of Ag-20.
Figure 24:
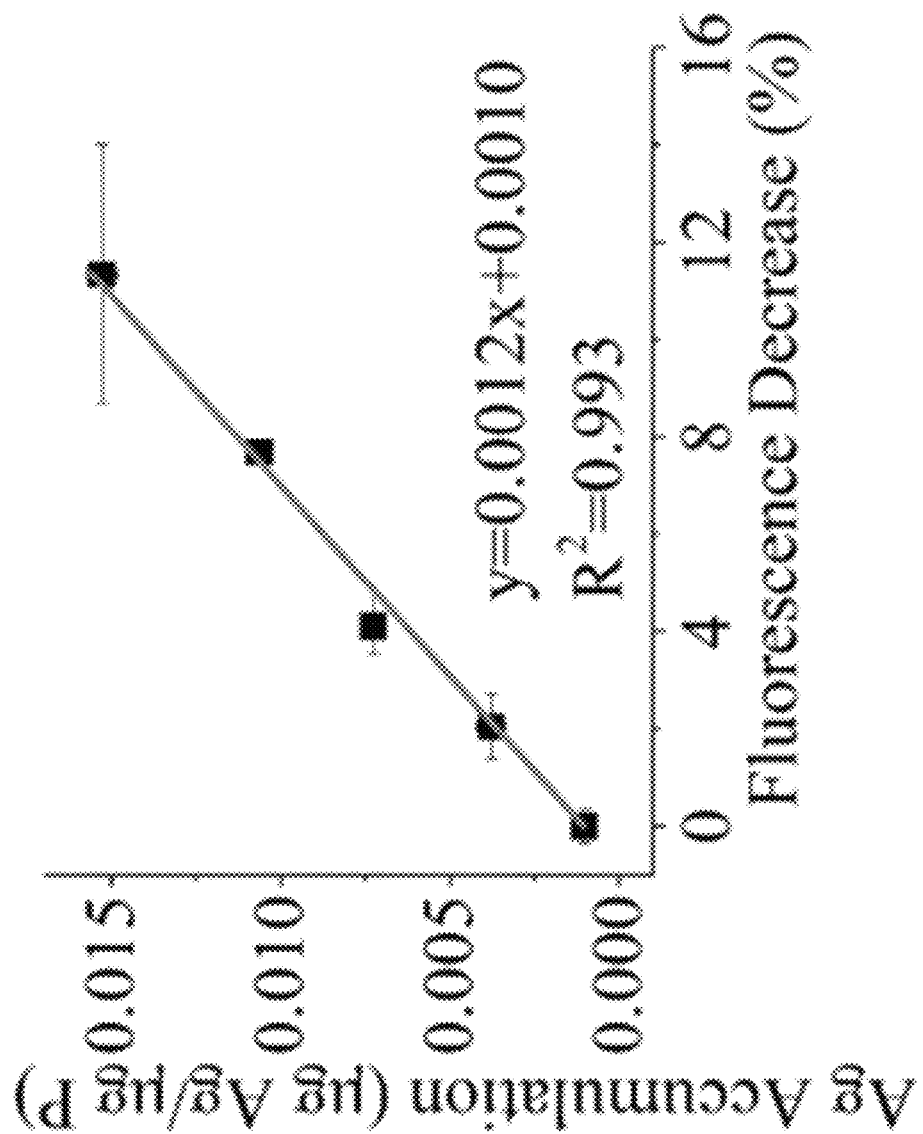
FIG. 24 is a graph showing the relationship between fluorescence decrease of Ade(-) yeast and total Ag accumulation.

Since the bioaccumulated Ag remained unchanged within 3 h (FIG. 17), the 3 h-detection procedure is as the followings (FIG. 19): 1. Obtain of Ade(−) yeast; 2. Co-culturing Ade(−) yeast with sample containing AgNPs and cysteine for 1 h; 3. Complete washing to remove the extracellular AgNPs and cysteine before the dissolution of internalized AgNPs to dissolve to $Ag^+$ intracellularly (1 h); 4. Addition of $Zn^{2+}$ at 0.05 µM for 1 h; 5. Detection of fluorescence by flow cytometry. FIG. 20 shows the close relationship between the concentration of AgNPs and fluorescence decrease from 0 to 75 µg/L ($R^2$=0.992), and this bio-collector could determine 7 nm AgNPs at concentration as low as 8.9 µg/L. Unlike the 7 nm AgNPs, the fluorescence decrease induced by 20 nm AgNPs did not change when the concentration of AgNPs was higher than 23.8 µg/L (FIG. 21). Independent of the size of AgNP, the fluorescence decrease was induced by Ag accumulation (FIG. 22 and FIG. 23). Unlike the accumulation of 7 nm AgNPs which increased to 15 ng Ag/pg P as the concentration of NP increased, the accumulation of 20 nm AgNPs increased to an unchanged value at approximate 8 ng Ag/pg P. FIG. 24 shows that the lowest accumulated Ag (ionic form) that could be determined was 3.77 ng Ag/pg P. Thus, even more 20 nm AgNPs were added to the medium, the bioavailable Ag remained unchanged at 8 ng Ag/pg P and no further dissolved Ag could be determined (or less than 3.77 ng Ag/pg P). The difference of fluorescence decrease caused by these two AgNPs was largely due to their different bioaccumulation capacities.

Figure 25:
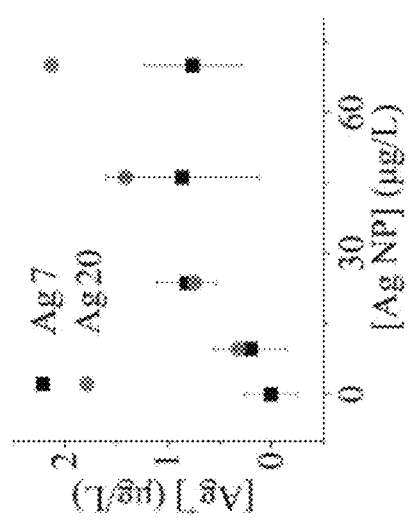
FIG. 25 is a graph showing the different bioeffect caused by Ag-7 and Ag-20.
Figure 26:
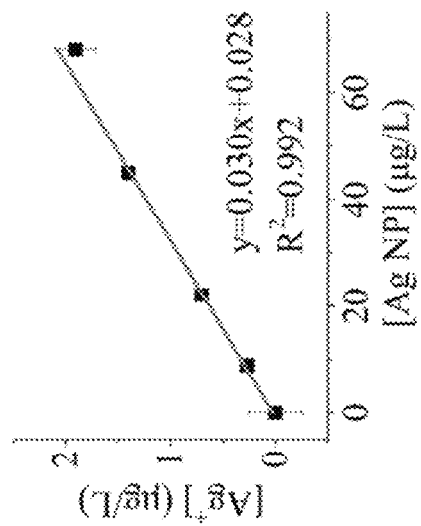
FIG. 26 is a graph showing the relationship between concentration of 7 nm AgNP and concentration of $Ag^+$.
Figure 27:
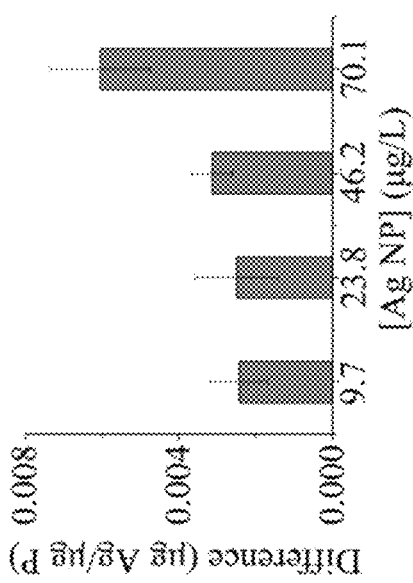
FIG. 27 is a graph showing difference in bioaccumulation of Ag from Ag-7 and Ag-20.
Figure 28:
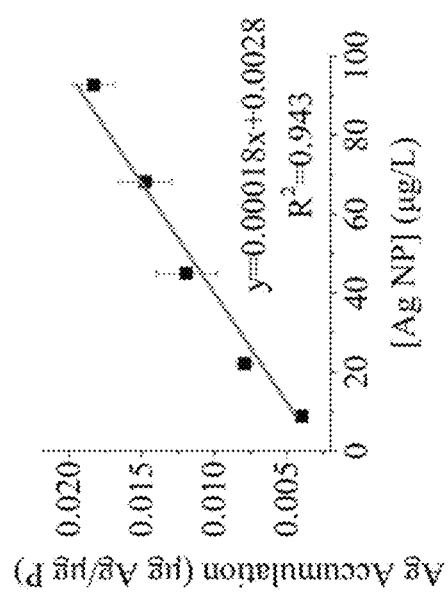
FIG. 28 is a graph showing the relationship between the concentration of 7 nm AgNP and accumulated Ag.

The decrease in fluorescence caused by $Ag^+$ as a bridge to connect the bioeffect of 7 nm AgNPs and 20 nm AgNPs (FIG. 25). Based on the linear relationship between the concentration of 7 nm AgNPs and [$Ag^+$] ($R^2$=0.992, FIG. 26), bioeffects (shown as the concentration of $Ag^+$ inducing the similar fluorescence decrease) of 7 nm AgNPs at 9.7/23.8/46.2/70.1 µg/L were calculated, and difference between 7 nm AgNPs and 20 nm AgNPs at the same concentration was compared (FIG. 27). The difference between these two groups became significant when the concentration of AgNPs was over 70.1 µg/L (FIG. 25), due to the increasing difference of accumulated Ag at higher concentrations (FIG. 27 and FIG. 28). When the concentration of AgNPs was lower than 70.1 µg/L, the difference of Ag accumulation between these two NPs treatments was less than 3.7 ng Ag/pg P, which was unable to be identified by this biosystem. These data suggested that due to the high bioaccumulation of small sized AgNPs, the biosystem was more suitable to collect the small AgNPs in the surroundings. In contrast, due to the limited internalization by yeast cells (cell size around 2-5 µm), the bioaccumulation of large AgNPs was nearly saturated at high concentrations.

Figure 29:
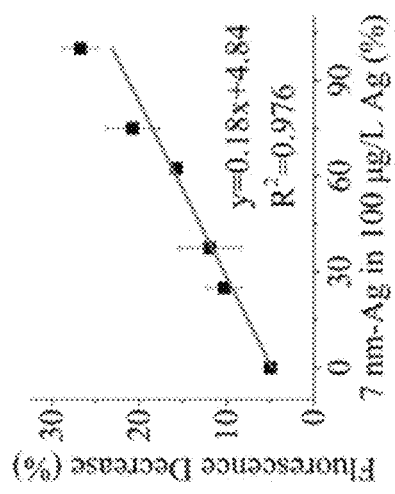
FIG. 29 is a graph showing the fluorescence decrease induced by 100 µg/L nano Ag.

FIG. 29 shows the bio-response of yeast to the mixture of AgNPs with mean diameter at 7 nm (4.5-9 nm) and at 20 nm (16-26 nm). (The x axis shows the concentration of 7 nm AgNPs in 100 µg/L total Ag. For example, if 30% of Ag are AgNPs at 7 nm, the left 70% of Ag are AgNPs at 20 nm.) The fluorescence decrease was stabilized to around 5% even the concentration of AgNPs (16-26 nm) was as high as 100 µg/L, which was consistent with the unchanged fluorescence decrease in FIG. 21. In contrast, the fluorescence decrease was enhanced as the percentage of small AgNPs (4.5-9 nm) increased from 0% to 100% ($R^2$=0.976, FIG. 29). Due to the limited bioaccumulation of large AgNPs, the small sized yeast cells could act as a screener to isolate the large AgNPs (>16 nm) from the smaller AgNPs, with the unchanged fluorescence intensity caused by isolated large NPs and only the internalized small NPs could make a difference on the fluorescence change. Compared with the large AgNPs, the cytotoxicity of small ones (<10 nm) was higher owing to the high bioavailability and high "Trojan horse effect" such as intracellular dissolution (Gliga et al., 2014). Therefore, this bio-collector system was suitable to determine the most toxic AgNPs in the environment. In contrast to our yeast based biosystem, SP-ICP-MS was limited by its size inclusion, and AgNPs with diameters smaller than 18 nm were difficult to be identified (Lee et al., 2014; Schaumann et al., 2015). Therefore, combing the use of SP-ICP-MS and yeast cells could further differentiate the ultra-small/most toxic AgNPs (<10 nm) from the total AgNPs (<20 nm) and the determination range of AgNPs using SP-ICP-MS could be broadened by the yeast cells.

Cellular Dissolution of AgNPs

Figure 30:
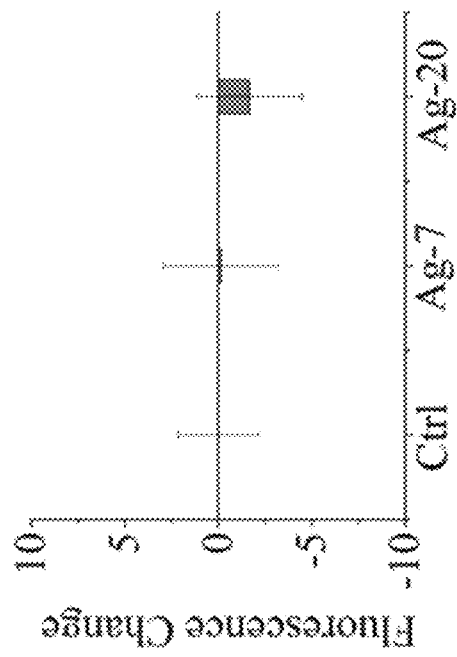
FIG. 30 is a graph showing a fluorescence change caused by nanoformed 7 nm AgNPs and 20 nm AgNPs.
Figure 31:
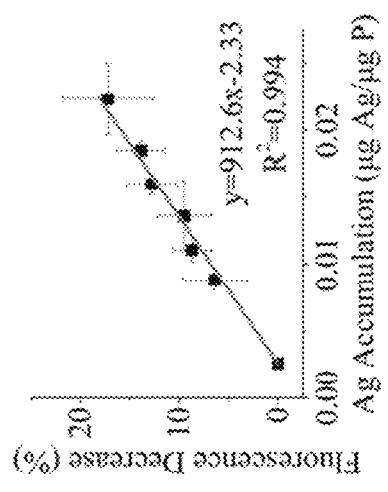
FIG. 31 is a graph showing the relationship between accumulated Ag and fluorescence decrease of Ade(-) yeast.
Figure 32:
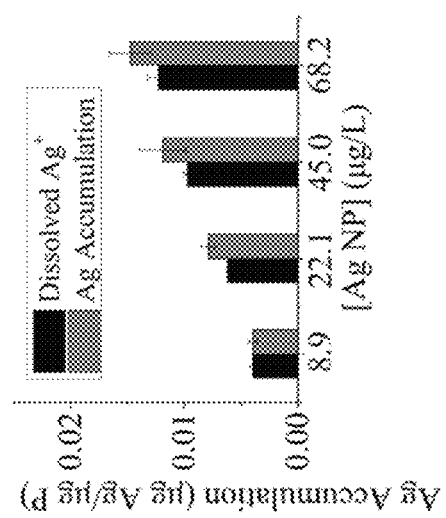
FIG. 32 is a graph showing the intracellular dissolution of 7 nm AgNPs.
Figure 33:
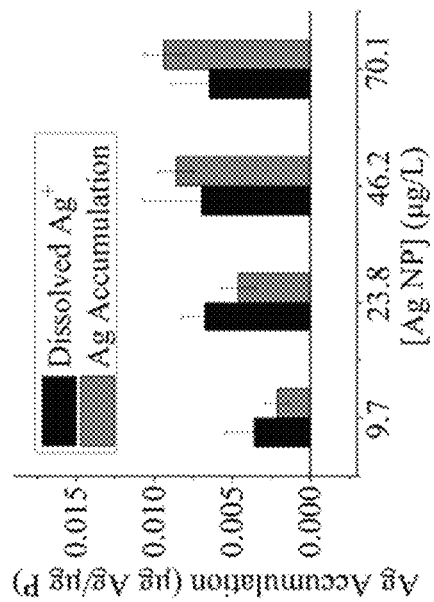
FIG. 33 is a graph showing the intracellular dissolution of 20 nm AgNPs.

Fluorescence change caused by AgNPs (using the highest 75 µg/L) was insignificant (FIG. 30), suggesting that the main factor inducing the fluorescence decrease of Ade(−) yeast was the $Ag^+$ as a result of cellular dissolution of AgNPs. Based on the relationship between fluorescence decrease and accumulation of $Ag^+$ ($R^2$=0.994, FIG. 31), the dissolved $Ag^+$ from the internalized AgNPs could be thus quantified. For the 7 nm AgNP treatment, most AgNPs were dissolved to $Ag^+$ (FIG. 32), and the obtained intracellular dissolution rates were higher than 78% when the concentration of added AgNPs at 8.9-68.2 µg/L. The high intracellular dissolution of 7 nm AgNPs (over 78%) was consistent with the result that particle size was the main factor affecting the solubility (Ma et al., 2012). The nanoparticle surface area determined the amount of released $Ag^+$ by influencing the rate of dissolution (Levard et al., 2012), resulting in the high dissolution rate of 7 nm AgNPs. In contrast to the increased dissolved $Ag^+$ with increasing concentration in the 7 nm AgNPs treatment, the dissolved $Ag^+$ was independent of the concentration of AgNPs (20 nm), even though the total accumulated Ag enhanced (FIG. 33). The result was consistent with the unchanged fluorescence decrease by 20 nm AgNPs (FIG. 21). Therefore, compared with the 7 nm AgNPs, the intracellular transformation of 20 nm AgNPs to $Ag^+$ was weaker, and the larger size of AgNPs may prefer to localize in the cytoplasm instead of digestive vacuoles. The diameters of AgNPs increased further after cell internalization due to the modification in cytoplasm (Bao et al., 2016). Vacuoles were the primary storage sites for the accumulated Ag in fungi and plants (Cvjetko et al., 2018). The vacuole-to-cell volume ratio of W303 yeast was measured to be around 10% (Chan and Marshall, 2014). Additionally, the vacuole morphology was sensitive to the ionic stress, leading to the vacuole fragmentation and further shrinking of vacuole size (Li and Kane, 2009). Thus, AgNPs at 20 nm might not be easily dissolved by vacuoles. The determined fluorescence decrease caused by the internalized Ag over 0.00377 µg Ag/pg P was more reliable, resulting in the large deviation of calculated dissolved $Ag^+$ in the 20 nm Ag NP group (FIG. 33).

Figure 34:
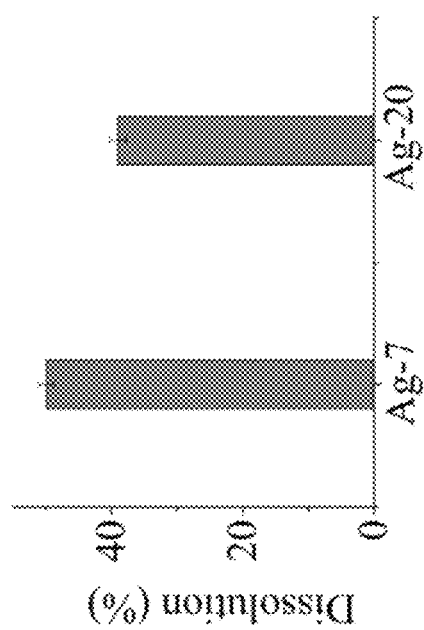
FIG. 34 is a graph showing the dissolution rate of AgNPs in media (pH=5.20).

The pH range of vacuole in the wild type of yeast was 5.0-6.0 (Martinez-Munoz and Kane, 2008). We further adjusted the pH value to 5.20 to simulate the environment of acidic vacuole. The resulting dissolution rates of 7 nm AgNPs and 20 nm AgNPs at 75 µg/L were around 50% and less than 40%, respectively (FIG. 34). The citrate coating is less stable than other coatings, resulting in the stripping of coatings from the particle surface along with $Ag^+$ in acidic solutions (Axson et al., 2015). Compared with AgNPs over 10 nm, the dissolution of Ag NPs less than 10 nm rapidly increased in acidic solutions (Molleman and Hiemstra, 2017). Due to the size related dissolution rate, such 10% difference of the dissolution rate might result in the difference of intracellular dissolution of AgNPs of different sizes. The acidic environment together with enzymes in vacuoles could result in a higher dissolution of AgNPs in Ade(−) yeast for the 7 nm AgNPs compared with the larger sized AgNPs.

Overall, the detection of AgNPs using this biosystem was mainly dependent on the amount of bioaccumulated AgNPs and the efficiency of intracellular dissolution of AgNPs. Due to the size dependent endocytosis and dissolution in acidic environment, the biosystem was more suitable to determine AgNPs with small size (7 nm). For larger size of AgNPs (e.g., 20 nm), limiting factors included the low bioaccumulation and the low intracellular dissolution. Taking advantage of this, the biosensor had the potential to differentiate ultra-small AgNPs from other AgNPs in the surroundings. Based on the fact that AgNPs with small diameters tended to dissolve more $Ag^+$ which was positively correlated with toxicity (Yang et al., 2011; Angel et al., 2013), yeast cells collected the most toxic and small ones, and subsequently induced high fluorescence decrease. In previous study, SP-ICP-MS was applied to differentiate AgNPs with different size distributions (e.g., 40 nm, 60 nm and 100 nm), with intensities induced by NPs less than 20 nm returning to the background levels (Mitrano et al., 2012). Combing with the use of SP-ICP-MS, the biosystem could complete the differentiation and improve the size resolution.

Based on the side effects of intracellularly dissolved $Ag^+$ on the $Zn^{2+}$ directed autofluorescence increase of the Ade(−) yeast, bioaccumulated $Ag^+$ at as low as 3.77 ng Ag/pg P could be determined using this biosensor. Limited interference by other metals and pH variations enabled its application to collect AgNPs from complicated matrix. Based on the bioaccumulation of AgNPs and intracellular dissolution of AgNPs in Ade(−) yeast, the biosensor collected the surrounding AgNPs and could quantify the 7 nm Ag NP at concentration as low as 8.9 µg/L. As low dose of AgNPs was used in this study, the fluorescence decrease caused by AgNPs was mainly related to the dissolved $Ag^+$ rather than to the particles. The intracellularly dissolved $Ag^+$ from internalized AgNPs was determined and the value was higher for small AgNPs compared with large ones. The higher intracellular dissolution and bioaccumulation of 7 nm AgNPs contributed to the better performance of Ade(−) yeast for ultra-small AgNPs, thus this biosensor could further differentiate ultra-small NPs (<10 nm) and large ones (<20 nm and differentiated by SP-ICP-MS). Our study for the first time proposed a yeast-based individual biosensor to quantify both AgNPs and dissolved $Ag^+$, expanding the application of yeast cells in the field of metal determination.

From the above illustrations, the present inventions show that a detection organism, and more specifically a yeast adapted to autofluorescence in the presence of zinc ions and de-fluoresce in the presence of silver ions (such as an adenine deficient yeast (Ade(−) yeast) can be used to quantify AgNPs by determining the intracellularly dissolved $Ag^+$. The method was based on the result that the autofluorescence increase of Ade(−) yeast was enhanced by $Zn^{2+}$ but decreased by $Ag^+$. Based on the bioaccumulation of ultra-small AgNPs by Ade(−) yeast and their intracellular dissolution, we used this biosystem to 'collect'/'concentrate' the surrounding AgNPs and quantify the extracellular AgNPs thereof. The intracellularly dissolved $Ag^+$ could thus be determined and compared with the total Ag accumulation. Our study for the first time proposed a yeast-based individual biosensor to determine both AgNPs and their intracellularly dissolved $Ag^+$ in aqueous suspension. The method had ultra-high sensitivity, low detection limit, and wide potential in environmental assessment based on biosensors.

Silver nanoparticles (AgNPs) are now being increasingly applied in many fields. It is useful to detect and quantify these nanoparticles as well as their cellular dissolution for biological assessment, for example. In an embodiment, the present invention has developed a novel approach to quantify the concentration of ultra-small AgNPs based on principally finding that dissolved $Ag^+$ decreased the $Zn^{2+}$ directed fluorescence increase of a detection organism such as an adenine deficient yeast [Ade(−) yeast]. To obtain the highest sensitivity to AgNPs, experiments were conducted to demonstrate that the biomass of the detection organism and addition of $Zn^{2+}$ are optimal at 0.005 and 0.05 µM, respectively. The experiments show that the lowest detectable $Ag^+$ dissolved from the internalized AgNPs is 3.77 ng Ag/µg P, and the lowest detectable concentration of AgNPs (average 7 nm in diameter) is 8.9 µg/L, while the bio-response induced by larger AgNPs (20 nm) does not change with an increasing AgNPs concentration. It can thus be demonstrated that the detection organism such as an Ade(−) yeast selectively collects the ambient ultra-small AgNPs and acts as a screener or bio-screener to differentiate small AgNPs (4.5-9 nm in diameter) and large ones (16-26 nm). The method can further be employed to determine the cellular dissolution of these ultra-small AgNPs once they are internalized by the detection organism (yeast cells). The experiments have shown that over 78% of the internalized 7 nm-AgNPs is dissolved to $Ag^+$. The present invention thus provides a means, i.e. a novel biosensor, using for example Ade(−) yeast in screening for ultra-small AgNPs from the larger ones and monitoring the cellular dissolution processes of these ultra-small AgNPs.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose.

REFERENCES

The following references are incorporated in their entirety and a skilled person is considered to be aware of disclosure of these references.

Angel, B. M., Batley, G. E., Jarolimek, C. V., Rogers, N. J., 2013. Chemosphere 93, 359-365.
Axson, J. L., Stark, D. I., Bondy, A. L., Capracotta, S. S., Maynard, A. D., Philbert, M. A., Bergin, I. L., Ault, A. P., 2015. J. Phys. Chem. C 35, 20632-20641.
Bao, D. P., Oh, Z. G., Chen, Z., 2016. Front. Plant Sci. 7, 1-8.
Benn, T. M., Westerhoff, P., 2008. Environ. Sci. Technol. 42, 4133-4139.
Blaser, S. A., Scheringer, M., Fau-Macleod, M., Macleod, M., Fau-HungerbOhler, K., Hungerbuhler, K., 2008. Sci. Total Environ. 390, 396-409.
Chan, Y. H. M., Marshall, W. F., 2014. Biophys. J. 106, 1986-1996.
Chao, J. B., Liu, J. F., Yu, S. J., Feng, Y. D., Tan, Z. Q., Liu, R., Yin, Y. G., 2011. Anal. Chem. 83, 6875-6882.
Choi, O., Clevenger, T. E., Deng, B., Surampalli, R. Y., Ross, L., Jr., Hu, Z., 2009. Water Res. 43, 1879-1886.
Cvjetko, P., Zovko, M., Štefanić, P. P., Biba, R., Tkalec, M., Domijan, A. M., Vrček, I. V., Papst, I. L., Šikić, S., Balen, B., 2018. Environ. Sci. & Pollut. Res. 25, 5590-5601.
Fabricius, A. L., Duester, L., Meermann, B., Ternes, T. A., 2014. Anal. Bioanal. Chem. 406, 467-479.
Gliga, A. R., Skoglund, S., Wallinder, I. O., Fadeel, B., Karlsson, H. L., 2014. Part. Fibre. Toxicol. 11, 11.
Hadioui, M., Peyrot, C., Wilkinson, K. J., 2014. Anal. Chem. 86, 4668-4674.
Hendren, C. O., Badireddy, A. R., Casman, E., Wiesner, M. R., 2013. Sci. Total. Environ. 449, 418-425.
Lee, S., Bi, X., Reed, R. B., Ranville, J. F., Herckes, P. and Westerhoff, P., 2014. Environ. Sci. Technol. 48, 10291-10300.
Levard, C., Hotze, E. M., Lowry, G. V., Jr, G. E. B., 2012. Environ. Sci. Technol. 46, 6900-6914.
Li, S. C., Kane, P. M., 2009. Biochim. Biophys. Acta, Mol. Cell Res. 1793, 650-663.
Liu, S., Tian, J., Wang, L., Sun, X., 2012. Sens. Actuators, B. 165, 44-47.
Lowry, G. V., Espinasse, B. P., Badireddy, A. R., Richardson, C. J., Reinsch, B. C., Bryant, L. D., Bone, A. J., Deonarine, A., Chae, S., Therezien, M., Colman, B. P., Hsu-Kim, H., Bernhardt, E. S., Matson, C. W., Wiesner, M. R., 2012. Environ. Sci. Technol. 46, 7027-7036.
Ma, R., Levard, C., Marinakos, S. M., Cheng, Y. W., Liu, J., Michel, F. M., Brown, G. E., Lowry, G. V., 2012. Environ. Sci. Technol. 46, 752-759.
Martinez-Munoz, G. A., Kane, P., 2008. J. Biol. Chem. 283, 20309-20319.
Mitrano, D. M., Barber, A., Bednar, A., Westerhoff, P., Higgins, C. P., Ranville, J. F., 2012. J. Anal. At. Spectrom. 27, 1131-1142.
Molleman, B., Hiemstra, T., 2017. Environ. Sci. Nano. 4, 1314-1327.
Mueller, N. C., Nowack, B., 2008. Environ. Sci. Technol. 42, 4447-4453.
Ni, P., Sun, Y., Dai, H., Hu, J., Jiang, S., Wang, Y., Li, Z., 2015. Biosens. Bioelectron. 63, 47-52.
Saran, R., Liu, J., 2016. Anal. Chem. 88, 4014-4020.
Schaumann, G. E., Philippe, A., Bundschuh, M., Metreveli, G., Klitzke, S., Rakcheev, D., Grun, A., Kumahor, S. K., Kuhn, M., Baumann, T., Lang, F., Manz, W., Schulz, R., Vogel, H. J., 2015. Sci. Total. Environ. 535, 3-19.
Shao, Z. S., Guagliardo, P., Jiang, H. B., Wang, W.-X., 2020. Environ. Sci. Technol. 55, 433-446.
Sun, A. Q., Wang, W.-X., 2021. Biosens. Bioelectron. 179, 113075.
Tuoriniemi, J., Comelis, G., Hassellov, M., 2012. Anal. Chem. 84, 3965-3972.
Yan, N., Tang, B. Z., Wang, W.-X., 2018a. ACS Nano. 12, 12212-12223.
Yan, N., Xie, S., Tang, B. Z., Wang, W.-X., 2018b. Chem. Commun. 54, 4585-4588.
Yan, N., Tang, B. Z., Wang, W.-X., 2021. Environ. Sci.: Nano.
Yang, X. Y., Gondikas, A. P., Marinakos, S. M., Auffan, M., Liu, J., Kim, H. H., Meyer, J. N., 2011. Environ. Sci. Technol. 46, 1119-1127.
Zhang, Z., Yan, J., 2014. Sens. Actuators, B. 202, 1058-1064.

What is claimed is:

1. A method for detection of presence and/or quantities of silver nanoparticles in a specimen when the silver nanoparticles have a size ranging from 4.5 to 9 nm or with an average size of 7 nm in diameter and the silver nanoparticles have a concentration of 8.9 to 75 µg/L, comprising:
providing a detection organism suspended in a medium and yielding a detection organism-suspended medium, wherein the detection organism auto-fluoresces in the presence of zinc ions and de-fluoresces in the presence of silver ions, wherein the detection organism is an adenine deficient *Saccharomyces cerevisiae*, and wherein the biomass of the adenine deficient yeast indicative of the concentration thereof in the detection organism-suspended medium ranges from $OD_{600}$=0.005 to $OD_{600}$=0.02,
treating the detection organism with zinc ions thus effecting auto-fluorescence therefrom, and then measuring a degree of fluorescence of the detection organism-suspended medium,
adding the specimen to the detection organism-suspended medium, treating the detection organism therein with the specimen for a period of time, and measuring a change of fluorescence of the detection organism-suspended medium over time,
calculating a concentration of silver ions intracellularly dissolved from the silver nanoparticles and accumulated in the detection organism in view of the change of fluorescence, and
extrapolating the concentration of silver nanoparticles in the specimen in view of the change of fluorescence and the concentration of the intracellularly dissolved silver ions.

2. The method as claimed in claim 1, wherein the *Saccharomyces cerevisiae* is strain W303.

3. The method as claimed in claim 2, wherein the adenine deficient *Saccharomyces cerevisiae* is a wildtype strain.

4. The method as claimed in claim 1, wherein the concentration of the intracellularly dissolved silver ions correlates to the concentration of the silver nanoparticles in the specimen.

5. The method as claimed in claim 4, wherein the method detects silver nanoparticles with an average size of 7 nm in diameter.

6. A method as claimed in claim 1, wherein the biomass of the adenine deficient yeast is $OD_{600}=0.005$.

7. The method as claimed in claim 1, wherein, treating the detection organism with zinc ions, comprises a step of optimizing the concentration of the zinc ions in the detection organism-suspended medium to 0.025-0.1 μM for at least 1 hour.

8. The method as claimed in claim 7, wherein the concentration of the zinc ions in the detection organism-suspended medium is optimized to 0.05 μM.

9. The method as claimed in claim 1, wherein the time period of the detection organism being treated with the specimen is 30-60 mins, and wherein measurement of the change in fluorescence is taken during and after the period of time.

10. The method as claimed in claim 9, wherein the period of time is 30 mins.

* * * * *